United States Patent
Boulet et al.

(10) Patent No.: US 7,410,982 B2
(45) Date of Patent: Aug. 12, 2008

(54) PROPANAMINE DERIVATIVES AS SEROTONIN AND NOREPINEPHRINE REUPTAKE INHIBITORS

(75) Inventors: Serge Louis Boulet, Fishers, IN (US); Sandra Ann Filla, Brownsburg, IN (US); Peter Thaddeus Gallagher, Basingstoke (GB); Kevin John Hudziak, Indianapolis, IN (US); Anette Margareta Johansson, Indianapolis, IN (US); Rushad E. Karanjawala, Zionsville, IN (US); John Joseph Masters, Fishers, IN (US); Brian Michael Mathes, Indianapolis, IN (US); Richard Edmund Rathmell, Basingstoke (GB); Maria Ann (nee Fagan) Whatton, Basingstoke (GB); Victor Matassa, Heidelberg (DE); Chad Nolan Wolfe, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 463 days.

(21) Appl. No.: 10/532,765

(22) PCT Filed: Oct. 24, 2003

(86) PCT No.: PCT/US03/31512

§ 371 (c)(1),
(2), (4) Date: Apr. 22, 2005

(87) PCT Pub. No.: WO2004/043931

PCT Pub. Date: May 27, 2004

(65) Prior Publication Data

US 2006/0058360 A1  Mar. 16, 2006

Related U.S. Application Data

(60) Provisional application No. 60/424,126, filed on Nov. 5, 2002.

(51) Int. Cl.
*A61K 31/4365* (2006.01)
*C07D 409/02* (2006.01)
(52) U.S. Cl. .................. 514/338; 546/281.1
(58) Field of Classification Search .......... 514/338; 546/281.1
See application file for complete search history.

(56) References Cited

U.S. PATENT DOCUMENTS 5,023,269 A  6/1991  Robertson et al.

FOREIGN PATENT DOCUMENTS

| EP | 0373836 A1 | 6/1990 |
|---|---|---|
| GB | 2 060 622 A | 5/1981 |
| WO | WO 02/094262 A1 | 11/2002 |
| WO | WO 2004/043904 A1 | 5/2004 |

OTHER PUBLICATIONS

King, Med Chem: Principle and Practice (1994), p. 206-208.*
David T. Wong et al., LY248686, A New Inhibitor of Serotonin and Norepinephrine Uptake, Neuropsychopharmacology, 1993, 23-33, vol. 8, No. 1.

* cited by examiner

*Primary Examiner*—Taofiq A Solola
(74) *Attorney, Agent, or Firm*—Robert D. Titus; Arvie J. Anderson

(57) ABSTRACT

There is provided a heteroaryloxy/thio 3-substituted propanamine compound of formula (I) wherein A is selected from —O— and —S—; X is selected from phenyl optionally substituted with up to 5 substituents each independently selected from halo, $C_1$-$C_4$ alkyl and $C_1$-$C_4$ alkoxy, thienyl optionally substituted with up to 3 substituents each independently selected from halo and $C_1$-$C_4$ alkyl, and $C_2$-$C_8$ alkyl, $C_2$-$C_8$ alkenyl, $C_3$-$C_8$ cycloalkyl and $C_4$-$C_8$ cycloalkylalkyl, each of which may be optionally substituted with up to 3 substituents each independently selected from halo, $C_1$-$C_4$ alkyl, $C_1$-$C_4$ alkoxy, $C_1$-$C_4$ alkyl —S(O)$_n$— where n is 0, 1 or 2, —CF$_3$, —CN and —CONH$_2$; Y is selected from dihydrobenzothienyl, benzothiazolyl, benzoisothiazolyl, quinolyl, isoquinolyl, naphthyridyl, and thienopyridyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-S(O)$_n$— where n is 0, 1 or 2, nitro acetyl, —CF$_3$, —SCF$_3$ and cyano; Z is selected from H, OR$_3$ or F, wherein R$_3$ is selected from H, $C_1$-$C_6$ alkyl and phenyl $C_1$-$C_6$ alkyl; R$_1$ and R$_2$ are each independently H or $C_1$-$C_4$ alkyl; and pharmaceutically acceptable salts thereof.

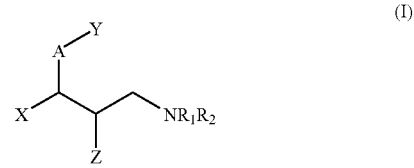

4 Claims, No Drawings

PROPANAMINE DERIVATIVES AS SEROTONIN AND NOREPINEPHRINE REUPTAKE INHIBITORS

This application is a United States national phase entry, pursuant to 35 U.S.C. 371, of PCT/US2003/031512, filed Oct. 24, 2003, which claims the benefit of U.S. provisional patent application Ser. No. 60/424,126, filed Nov. 5, 2002.

This invention relates to novel heteroaryloxy/thio 3-substituted propanamines, and to their use in inhibiting serotonin and norepinephrine reuptake.

Serotonin (5-HT) has been implicated in the aetiology of many disease states and has been found to be of importance in mental illnesses, depression, anxiety, schizophrenia, eating disorders, obsessive compulsive disorder (OCD) and migraine. Indeed many currently used treatments of these disorders are thought to act by modulating serotonergic tone. During the last decade, multiple serotonin receptor subtypes have been characterized. This has led to the realisation that many treatments act via the serotonergic system, such as selective serotonin reuptake inhibitor (SSRI) antidepressants which increase serotonin transmission, such as, for example, the hydrochloride salt of fluoxetine.

Drugs that exert their main action on the norepinephrinergic system have been available for some time, however their lack of selectivity made it difficult to determine specific clinical effects produced by a selective action on norepinephrine reuptake. Accumulating evidence indicates that the norepinephrinergic system modulates drive and energy, whereas the serotonergic system modulates mood. Thus norepinephrine appears to play an important role in the disturbances of vegetative function associated with affective, anxiety and cognitive disorders. Atomoxetine hydrochloride is a selective inhibitor of norepinephrine, and is currently marketed for the treatment of attention deficit hyperactivity disorder (ADHD).

Norepinephrine and serotonin receptors are known to interact anatomically and pharmacologically. Compounds that affect only serotonin have been shown to exhibit modulatory effects on norepinephrine, pointing toward an important relationship between the two neurotransmitter systems.

Duloxetine, (+)-N-methyl-3-(1-naphthalenyloxy)-2-thiophenepropanamine hydrochloride, inhibits the reuptake of both norepinephrine and serotonin, and is currently under development for the treatment of depression and urinary incontinence. The compound duloxetine was disclosed in U.S. Pat. Nos. 5,023,269 and 4,956,388.

U.S. Pat. No. 4,018,895 describes aryloxyphenyl propanamine compounds including compounds of the formula

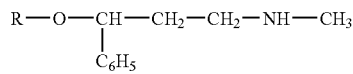

Where R is, for example, phenyl, substituted phenyl, tolyl or anisyl. The compounds block the uptake of various physiologically active monoamines including serotonin, norepinephrine and dopamine. Some of the compounds are selective to one of the monoamines and others have multiple activity. The compounds are indicated as psychotropic agents. Some are also antagonists of apomorphine and/or reserpine.

WO 00/02551 describes inter alia 3-aryloxy-3-substituted propanamines which are active at the NMDA receptor and serotonin reuptake site.

WO 97/45115 describes compounds which inhibit glycine transport via the GlyT-1 or GlyT-2 transporters. Some of the compounds disclosed are 3-aryloxy-3-phenyl-substituted propanamines although they also possess further N-substitution by, for example, CH2(CO2)Et.

EP 0318727 and EP 0399504 disclose certain aryloxyphenylpropanamines for use as calcium antagonists.

WO 01/62714 discloses phenylheteroalkylamine derivatives which are inhibitors of nitric oxide synthase. WO 03/011831 and WO 03/011830 discloses heteroarylheteroalkylamine derivatives which are inhibitors of nitric oxide synthase.

WO 02/094262 discloses heteroaryloxy 3-substituted propanamines as serotonin and norepinephrine reuptake inhibitors.

The present invention provides novel heteroaryloxy/thio propanamines which are potent inhibitors of both serotonin and norepinephrine reuptake. Preferred compounds of the present invention exhibit (i) greater potency of inhibition of the serotonin and/or morepinephrine transporters; and/or (ii) improved selectivity of inhibition of the serotonin and/or norepinephrine transporters relative to the dopamine transporter, and/or (iii) improved ADME properties (e.g. reduced tendency to act as a substrate and/or inhibitor the enzyme Cytochrome P450 2D6), and/or (iv) improved acid stability, as compared known inhibitors of both serotonin and norepinephrine reuptake.

According to the present invention there is provided a compound of formula I:

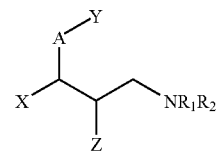

wherein

A is selected from —O— and —S—;

X is selected from phenyl optionally substituted with up to 5 substituents each independently selected from halo, $C_1$-$C_4$ alkyl and $C_1$-$C_4$ alkoxy, thienyl optionally substituted with up to 3 substituents each independently selected from halo and $C_1$-$C_4$ alkyl, and $C_2$-$C_8$ alkyl, $C_2$-$C_8$ alkenyl, $C_3$-$C_8$ cycloalkyl and $C_4$-$C_8$ cycloalkylalkyl, each of which may be optionally substituted with up to 3 substituents each independently selected from halo, $C_1$-$C_4$ alkyl, $C_1$-$C_4$ alkoxy, $C_1$-$C_4$ alkyl-S(O)n— where n is 0, 1 or 2, —$CF_3$, —CN and —$CONH_2$;

Y is selected from dihydrobenzothienyl, benzothiazolyl, benzoisothiazolyl, quinolyl, isoquinolyl, naphthyridyl, and thienopyridyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-S(O)$_n$— where n is 0, 1 or 2, nitro, acetyl, —$CF_3$, —$SCF_3$ and cyano;

Z is selected from H, O$R_3$ or F, wherein $R_3$ is selected from H, $C_1$-$C_6$ alkyl and phenyl $C_1$-$C_6$ alkyl;

$R_1$ and $R_2$ are each independently H or $C_1$-$C_4$ alkyl;

and pharmaceutically acceptable salts thereof.

The compounds of the present invention are potent and selective inhibitors of serotonin and norepinephrine reuptake.

In one group of compounds according to the present invention, A is —O—.

In another group of compounds according to the present invention, A is —S—.

Preferably, one of $R_1$ and $R_2$ is H.

$R_1$ and $R_2$ may both be H. Alternatively, one of $R_1$ and $R_2$ may be H while the other is $C_1$-$C_4$ alkyl, for example $C_1$-$C_3$ alkyl. Preferably, one of $R_1$ and $R_2$ is H and the other is methyl.

It will be appreciated that a compound of formula I will possess at least one or, when Z is not H, at least two chiral centres. Where a structural formula does not specify the stereochemistry at one or more chiral centres, it encompasses all possible stereoisomers and all possible mixtures of stereoisomers (including, but not limited to, racemic mixtures) which may result from stereoisomerism at each of the one or more chiral centers.

In one embodiment of the present invention, the compound possesses the stereochemistry defined in formula II

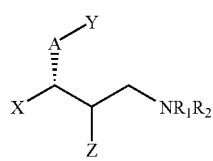

II

In another embodiment of the present invention, the compound possesses the stereochemistry defined in formula III

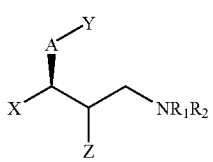

III

In another embodiment of the present invention, Z is H.

In one embodiment of the present invention, X is unsubstituted phenyl or phenyl which is mono- di- or tri-substituted with substituents independently selected from halo, $C_1$-$C_4$ alkyl and/or $C_1$-$C_4$ alkoxy. Halo substituents include F, Cl, Br and I, preferably F or Cl. Preferably, X is unsubstituted phenyl or phenyl which is mono-substituted with fluorine.

When X in formula I above is substituted thienyl, it is preferably mono-, di- or tri-substituted. Halo substituents include F, Cl, Br and I, preferably F or Cl. Suitable $C_1$-$C_4$ alkyl substituents include unsubstituted straight or branched alkyl groups of 1, 2, 3 or 4 carbon atoms, preferably methyl. When X is thienyl it is preferably thien-2-yl.

In one embodiment of the present invention, Y is dihydrobenzothienyl optionally substituted with up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano. In this embodiment, Y is preferably unsubstituted dihydrobenzothienyl or dihydrobenzothienyl which is mono-substituted with fluorine, preferably at the 4-position.

In one embodiment of the present invention, Y is benzothiazolyl or benzoisothiazolyl, each of which may be optionally substituted with up to 4 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano. In this embodiment, Y is preferably unsubstituted benzothiazolyl, unsubstituted benzoisothiazolyl, benzothiazolyl which is mono-substituted with $CH_3$ (preferably in the 4- or 7-position) or benzoisothiazolyl which is mono-substituted with $CH_3$ (preferably in the 4- or 7-position).

In one embodiment of the present invention, Y is thienopyridyl optionally substituted with up to 4 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano. In this embodiment, Y is preferably unsubstituted thienopyridyl, more preferably selected from thieno-[2,3-b]pyridinyl, thieno-[2,3-c]pyridinyl, thieno-[3,2-c]pyridinyl and thieno-[3,2-b]pyridinyl with thieno-[3,2-b]pyridinyl and thieno-[3,2-c]pyridinyl being most preferred.

In the embodiments described above wherein Y is dihydrobenzothienyl, benzothiazolyl, benzoisothiazolyl or thienopyridyl, each of which being optionally substituted as described above, the preferred point of attachment of the group Y to the —O— or —S— atom is attachment at the 4 or 7 position.

In one embodiment of the present invention, Y is quinolyl, isoquinolyl or naphthyridyl, each of which may be optionally substituted with up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano. In this embodiment, Y is preferably unsubstituted quinolyl, isoquinolyl or naphthyridyl. When Y is unsubstituted naphthyridyl it is preferably selected from 1,5-, 1,6-, 1,7- and 1,8-naphthyridyl with 1,7-naphthyridyl being most preferred.

In the embodiments described above wherein Y is quinolyl, isoquinolyl or naphthyridyl, the preferred point of attachment of the group Y to the —O— or —S— atom is attachment at the 4, 5 or 6 position.

The present invention also provides sub-groups of compounds of formula I or II or III:

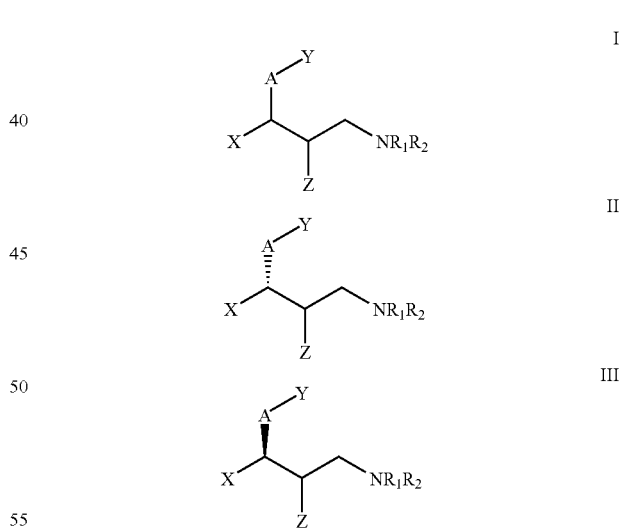

wherein

A is selected from —O— and —S—;

X is selected from phenyl optionally substituted with up to 5 substituents each independently selected from halo, $C_1$-$C_4$ alkyl and $C_1$-$C_4$ alkoxy, and thienyl optionally substituted with up to 3 substituents each independently selected from halo and $C_1$-$C_4$ alkyl;

Y is selected from dihydrobenzothienyl, benzothiazolyl, benzoisothiazolyl, quinolyl, isoquinolyl, naphthyridyl, and thienopyridyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano;

Z is selected from H, $OR_3$ or F, wherein $R_3$ is selected from H, $C_1$-$C_6$ alkyl and phenyl $C_1$-$C_6$ alkyl;

$R_1$ and $R_2$ are each independently H or $C_1$-$C_4$ alkyl;

and pharmaceutically acceptable salts thereof.

The present invention also provides sub-groups of compounds of formula I or II or III:

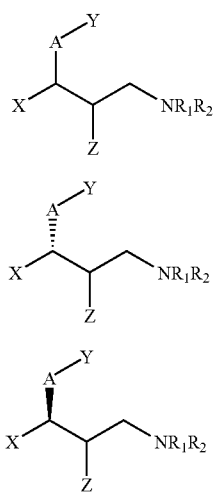

wherein

A is selected from —O— and —S—;

X is selected from phenyl optionally substituted with up to 5 substituents each independently selected from halo, $C_1$-$C_4$ alkyl and $C_1$-$C_4$ alkoxy, and thienyl optionally substituted with up to 3 substituents each independently selected from halo and $C_1$-$C_4$ alkyl;

Y is selected from dihydrobenzothienyl, benzothiazolyl, benzoisothiazolyl, quinolyl, isoquinolyl, naphthyridyl, and thienopyridyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano;

Z is H;

$R_1$ and $R_2$ are each independently H or $C_1$-$C_4$ alkyl;

and pharmaceutically acceptable salts thereof.

The present invention also provides sub-groups of compounds of formula I or II or III:

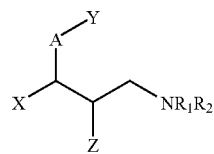

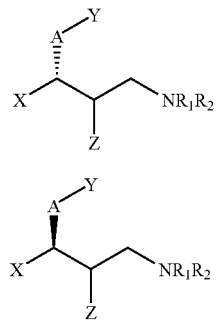

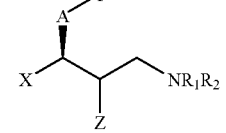

wherein

A is selected from —O— and —S—;

X is phenyl optionally substituted with up to 5 substituents each independently selected from halo, $C_1$-$C_4$ alkyl and $C_1$-$C_4$ alkoxy;

Y is selected from dihydrobenzothienyl, benzothiazolyl, benzoisothiazolyl, quinolyl, isoquinolyl, naphthyridyl, and thienopyridyl, each of which may be optionally substituted with up to 4 or, where possible, up to 5 substituents each independently selected from halo, $C_1$-$C_4$ alkyl, $C_1$-$C_4$ alkoxy, $C_1$-$C_4$ alkyl-$S(O)_n$— where n is 0, 1 or 2, nitro, acetyl, —$CF_3$, —$SCF_3$ and cyano;

Z is H;

$R_1$ and $R_2$ are each independently H or $C_1$-$C_4$ alkyl;

and pharmaceutically acceptable salts thereof.

The present invention also provides sub-groups of compounds of formula I or II or III:

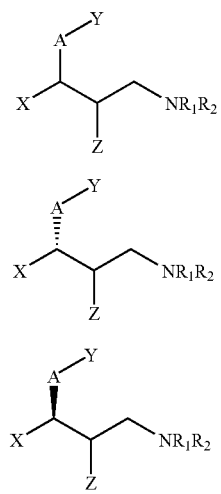

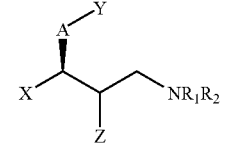

wherein

A is —O—;

X is phenyl optionally substituted with up to 5 substituents each independently selected from halo, $C_1$-$C_4$ alkyl and $C_1$-$C_4$ alkoxy;

Y is selected from dihydrobenzothienyl, benzothiazolyl, benzoisothiazolyl, quinolyl, isoquinolyl, naphthyridyl, and thienopyridyl, each of which may be optionally monosubstituted with halo, $C_1$-$C_4$ alkyl, $C_1$-$C_4$ alkoxy, —$CF_3$, or cyano;

Z is H;
R₁ and R₂ are each independently H or $C_1$-$C_4$ alkyl;
and pharmaceutically acceptable salts thereof.

The present invention also provides sub-groups of compounds of formula I or II or III:

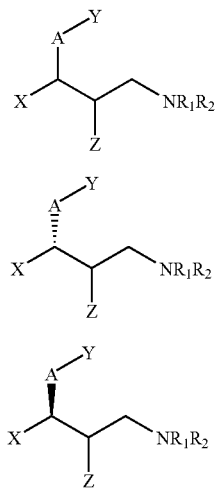

wherein
A is —O—;
X is phenyl optionally mono-substituted with fluorine;
Y is selected from dihydrobenzothienyl, benzothiazolyl, benzoisothiazolyl, quinolyl, isoquinolyl, naphthyridyl, and thienopyridyl, each of which may be optionally mono-substituted with fluoro or methyl;
Z is H;
R₁ is H and R₂ is methyl;
and pharmaceutically acceptable salts thereof.

In the present specification the term "$C_2$-$C_8$ alkyl" means a monovalent unsubstituted saturated straight-chain or branched-chain hydrocarbon radical having from 2 to 8 carbon atoms.

In the present specification the term "$C_2$-$C_8$ alkenyl" means a monovalent unsubstituted unsaturated straight-chain or branched-chain hydrocarbon radical having from 2 to 8 carbon atoms.

In the present specification the term "$C_3$-$C_8$ cycloalkyl" means a monovalent unsubstituted saturated cyclic hydrocarbon radical having from 3 to 8 carbon atoms.

In the present specification the term "$C_4$-$C_8$ cycloalkylalkyl" means a monovalent unsubstituted saturated cyclic hydrocarbon radical having from 3 to 7 carbon atoms linked to the point of substitution by a divalent unsubstituted saturated straight-chain or branched-chain hydrocarbon radical having at least 1 carbon atom.

In the present specification the term "halo" or "halogen" means F, Cl, Br or I.

In the present specification the term "$C_1$-$C_4$ alkoxy" means a monovalent unsubstituted saturated straight-chain or branched-chain hydrocarbon radical having from 1 to 4 carbon atoms linked to the point of substitution by an O atom.

In the present specification the term "phenyl $C_1$-$C_6$ alkyl" means a monovalent phenyl radical linked to the point of substitution by a divalent unsubstituted saturated straight-chain or branched-chain hydrocarbon radical having from 1 to 6 carbon atoms.

In the above definitions, similar terms specifying different numbers of C atoms take an analogous meaning.

In the present specification the term "dihydrobenzothienyl" includes 2,3-dihydrobenzothienyl and 1,3-dihydrobenzothienyl. 2,3-dihydrobenzothienyl is preferred.

In the present specification the term "benzoisothiazolyl" includes 1,2-benzoisothiazolyl and 2,1-benzoisothiazolyl. 1,2-benzoisothiazolyl is preferred.

In the present specification the term "naphthyridyl" includes 1,5-, 1,6-, 1,7- and 1,8-naphthyridyl. 1,7- naphthyridyl is preferred.

In the present specification the term "thienopyridyl" includes thieno-[2,3-b]pyridinyl, thieno-[2,3-c]pyridinyl, thieno-[3,2-c]pyridinyl and thieno-[3,2-b]pyridinyl. Thieno-[3,2-b]pyridinyl and thieno-[3,2-c]pyridinyl are preferred.

In the present specification the abbreviation "Ace-Cl" stands for α-chloroethyl chloroformate.

In the present specification the abbreviation "PS-DIPEA" stands for polymer-supported diisopropylethylamine.

The present invention also provides a process for producing a compound of formula I above, or a pharmaceutically acceptable salt thereof, which comprises reacting a compound of the formula IV:

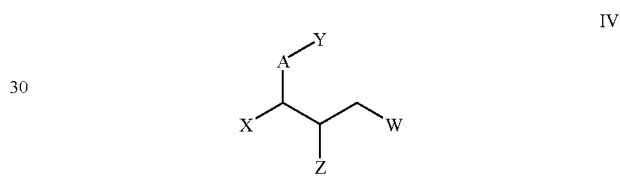

where A, X, Y and Z are as formula I above, and W is a leaving group, with an amine NR₁R₂ where R₁ and R₂ are as formula I above, optionally followed by the step of forming a pharmaceutically acceptable salt. Examples of suitable leaving groups include halo, mesylate and tosylate, but the nature of the leaving group is not critical. The reaction may be carried out in a sealed vessel with a lower alkyl alcohol as solvent.

The present invention also provides a process for producing a compound of formula I above wherein R₂ is H, or a pharmaceutically acceptable salt thereof, which comprises deprotecting a compound of the formula V

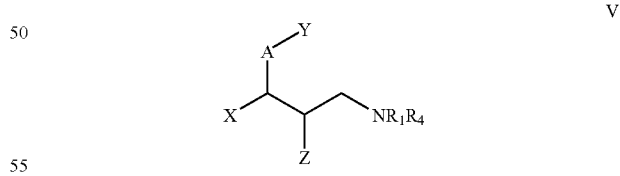

where A, X, Y, Z and R₁ are as formula I above, and R₄ is a suitable N-protecting group, optionally followed by the step of forming a pharmaceutically acceptable salt. Examples of suitable N-protecting groups will be known to the person skilled in the art and include, for example, benzyl and t-butoxycarbonyl.

The present invention also provides a process for producing a compound of formula I above wherein Z is OH, or a pharmaceutically acceptable salt thereof, which comprises reacting a compound of the formula VI

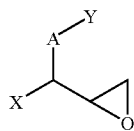

VI where A, X and Y are as formula I above with an amine $NR_1R_2$ where $R_1$ and $R_2$ as as formula I above, optionally followed by the step of forming a pharmaceutically acceptable salt.

The present invention also provides a process for producing a compound of formula I above wherein $R_1$ and $R_2$ are H, or a pharmaceutically acceptable salt thereof, which comprises reducing a compound of the formula VII:

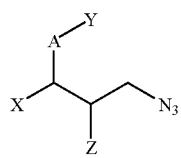

VII where A, X, Y and Z are as formula I above, optionally followed by the step of forming a pharmaceutically acceptable salt. Examples of suitable reducing agents will be known to the person skilled in the art.

The present invention also provides a process for producing a compound of formula I above wherein $R_1$ and $R_2$ are $C_1$-$C_4$ alkyl, or a pharmaceutically acceptable salt thereof, which comprises N-protecting a compound of the formula VIII by the introduction of two $C_1$-$C_4$ alkyl groups:

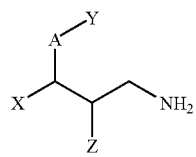

VIII where A, X, Y and Z are as formula I above, optionally followed by the step of forming a pharmaceutically acceptable salt. Examples of suitable reagents for effecting N-protection by two $C_1$-$C_4$ alkyl groups will be known to the person skilled in the art.

Compounds of the present invention are selective inhibitors of the reuptake of both serotonin and norepinephrine and as such are useful as pharmaceuticals. They are particularly useful for the treatment of pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and chronic pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

Current therapies for persistent pain include opiates, barbiturate-like drugs such as thiopental sodium and surgical procedures such as neurectomy, rhizotomy, cordotomy, and cordectomy.

The compounds of the present invention are indicated in the treatment of persistent pain and references herein to pain are intended to refer to persistent pain.

In addition to the compounds of formula I and processes for the preparation of said compounds, the present invention further provides pharmaceutical compositions comprising a compound of formula I or a pharmaceutically acceptable salt thereof, together with a pharmaceutically acceptable diluent or carrier.

Further, the present invention provides a compound of formula I or a pharmaceutically acceptable salt thereof, for use as a pharmaceutical; and a compound of formula I or a pharmaceutically acceptable salt thereof, for use as a selective inhibitor of the reuptake of both serotonin and norepinephrine.

The present compounds and salts may be indicated in the treatment of disorders associated with serotonin and norepinephrine dysfunction in mammals.

The term "serotonin and norepinephrine dysfunction" as used herein refers to a reduction in the amount of serotonin and norepinephrine neurotransmitters within the synaptic cleft below that which would be considered to be normal or desirable for a species, or an individual within that species. Thus the phrase "disorders associated with serotonin and norepinephrine dysfunction in mammals" refers to disorders which are associated with a reduction in the amount of serotonin and norepinephrine neurotransmitters within the synaptic cleft below that which would be considered to be normal or desirable for the mammalian species, or an individual within the species, in question. Some examples of disorders currently believed to be associated with reduced levels of serotonin and norepinephrine within the synaptic cleft include depression, OCD, anxiety, memory loss, urinary incontinence (including stress urinary incontinence and urge incontinence), conduct disorders, attention-deficit disorder (including ADHD), obesity, hot flushes/flashes, pain (including inflammatory pain, neuropathic pain, non-neuropathic non-inflammatory pain, persistent pain, persistent pain of inflammatory and/or neuropathic origin, headache and migraine), eating disorders (including bulimia and anorexia nervosa), inflammatory bowel disorders, functional bowel disorders, dyspepsia, chron's disease, iletis, ischemic bowel disease, ulcerative colitis, gastroesophageal reflux for functional bowel disorders, irritable bowel syndrome, insterstitial cystitis, urethral syndrome, gastric motility disorders, substance abuse (including alcoholism, tobacco abuse, smoking cessation, symptoms caused by withdrawal or partial withdrawal from the use of tobacco or nicotine and drug addiction including cocaine abuse), dementia of ageing, senile dementia, Alzheimer's, Parkinsonism, social phobia, disruptive behavior disorders, impulsive control disorders, borderline personality disorder, chronic fatigue syndrome, panic disorders, post-traumatic stress disorder, schizophrenia, gastrointestinal disorders, cardiovascular disorders, emesis, sleep disorders, cognitive disorders, psychotic disorders, brain trauma, premenstrual syndrome or late luteal syndrome, sexual dysfunction (including premature ejaculation and erectile difficulty), autism, mutism and trichotilomania. The compounds of the present invention are particularly suitable for the treatment of pain.

The compounds of the present invention are also indicated for the treatment of disorders which are ameliorated by an increase in the amount of serotonin and norepinephrine neurotransmitters within the synaptic cleft of a mammal above that which would be considered to be normal or desirable for the mammalian species, or an individual within the species, in question.

The term "treatment" as used herein refers to both curative and prophylactic treatment of disorders associated with norepinephrine dysfunction.

The present invention also provides the use of a compound of formula I, or a pharmaceutically acceptable salt thereof, in the manufacture of a medicament for selectively inhibiting the reuptake of serotonin and norepinephrine; the use of a compound of formula I, or a pharmaceutically acceptable salt thereof, in the manufacture of a medicament for the treatment of disorders associated with serotonin and norepinephrine dysfunction in mammals; the use of a compound of formula I, or a pharmaceutically acceptable salt thereof, in the manufacture of a medicament for the treatment of a disorder selected from those listed above and in particular selected from depression, OCD, anxiety, memory loss, urinary incontinence, conduct disorders, ADHD, obesity, alcoholism, smoking cessation, hot flushes/flashes and pain; and the use of a compound of formula I, or a pharmaceutically acceptable salt thereof, in the manufacture of a medicament for the treatment of a disorder selected from depression, urinary incontinence, particularly stress induced urinary incontinence, and more especially, pain. The present invention further provides a compound of formula I for treating disorders associated with serotonin and norepinephrine dysfunction in mammals, for example a disorder selected from those listed above and in particular selected from depression, OCD, anxiety, memory loss, urinary incontinence, conduct disorders, ADHD, obesity, alcoholism, smoking cessation, hot flushes/flashes and pain, especially depression, urinary incontinence, particularly stress induced urinary incontinence, and, more especially, pain.

Further the present invention provides a method for selectively inhibiting the reuptake of serotonin and norepinephrine in mammals, comprising administering to a patient in need thereof an effective amount of a compound of formula I or a pharmaceutically acceptable salt thereof; a method for treating disorders associated with serotonin and norepinephrine dysfunction in mammals, comprising administering to a patient in need thereof an effective amount of a compound of formula I or a pharmaceutically acceptable salt thereof; and a method for treating a disorder selected from those listed above and in particular selected from depression, OCD, anxiety, memory loss, urinary incontinence, conduct disorders, ADHD, obesity, alcoholism, smoking cessation, hot flushes/flashes and pain, comprising administering to a patient in need thereof an effective amount of a compound of formula I or a pharmaceutically acceptable salt thereof.

The present invention includes the pharmaceutically acceptable salts of the compounds of formula L. Suitable salts include acid addition salts, including salts formed with inorganic acids, for example hydrochloric, hydrobromic, nitric, sulphuric or phosphoric acids, or with organic acids, such as organic carboxylic acids, for example pyruvic, lactobionic, glycolic, oxalic, maleic, hydroxymaleic, fumaric, malic, tartaric, citric, salicylic, o-acetoxybenzoic, or organic sulphonic, 2-hydroxyethane sulphonic, toluene-p-sulphonic, bisethanesulphonic acid or methanesulphonic acid.

In addition to the pharmaceutically acceptable salts, other salts are included in the invention. They may serve as intermediates in the purification of compounds or in the preparation of other, for example pharmaceutically acceptable, acid addition salts, or are useful for identification, characterization or purification.

While all the compounds of the present invention are believed to inhibit the reuptake of serotonin and norepinephrine in mammals there are certain of these compounds which are preferred for such uses. Preferred values for A, X, Y, Z, $R_1$ and $R_2$ and substituents for each have been set out above.

Compounds of the present invention may be prepared by conventional organic chemistry techniques.

Where Z is H and X is phenyl the chiral alcohols are commercially available from the Aldrich Chemical Company in pure enantiomeric form and can be used without further purification. Additionally, the chloropropanols which are commercially available from the Aldrich Chemical Company may be converted via a Finkelstein reaction using sodium iodide in acetone under reflux conditions to the corresponding iodopropanols and these may be used as an alternative to the chloropropanols.

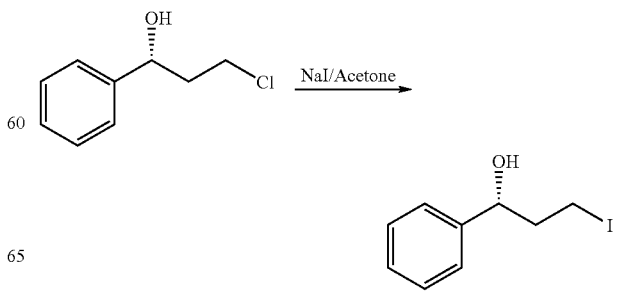

-continued

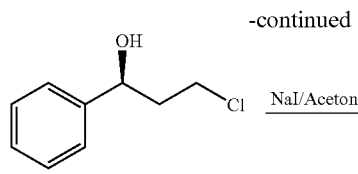

Where Z is H and X is thienyl the corresponding thienylpropanols can typically be prepared generally as follows (W is as defined above):

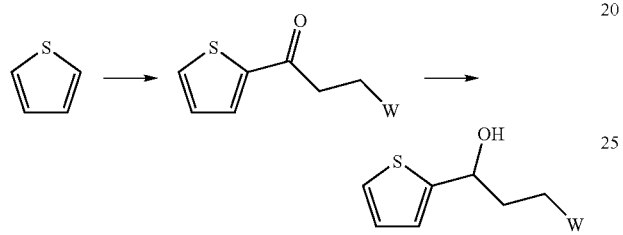

Subjecting thiophene to classical Friedel-Crafts acylation with an acid chloride such as chloropropionyl chloride in roughly equal quantities, with a strong Lewis acid such as aluminium chloride in a non-protic solvent such as dichloromethane or dichloroethane at temperatures ranging from −5° C. to reflux can result in the desired thienyl ketone. This ketone can be readily reduced to the desired alcohol either racemically using standard reducing agents such as sodium borohydride in a protic solvent such as the lower order alkyl alcohols, or Borane-THF complex in a polar non-protic solvent such as diethyl ether or THF. Chiral reduction of the ketone can be performed using a boron based chiral reducing agent in which high enantiomeric excesses can be obtained. Further details regarding this procedure can be found in J. Labelled Compd. Rad., 1995, 36, (3), 213 and references therein.

Where Z is H and X is selected from $C_2$-$C_8$ alkyl, $C_2$-$C_8$ alkenyl, $C_3$-$C_8$ cycloalkyl and $C_4$-$C_8$ cycloalkylalkyl, the corresponding 1-X, 3-aminopropanols can be prepared via the corresponding 3-amino-N-methoxy-N-methylpropanamide, known as a Weinreb amide, as follows:

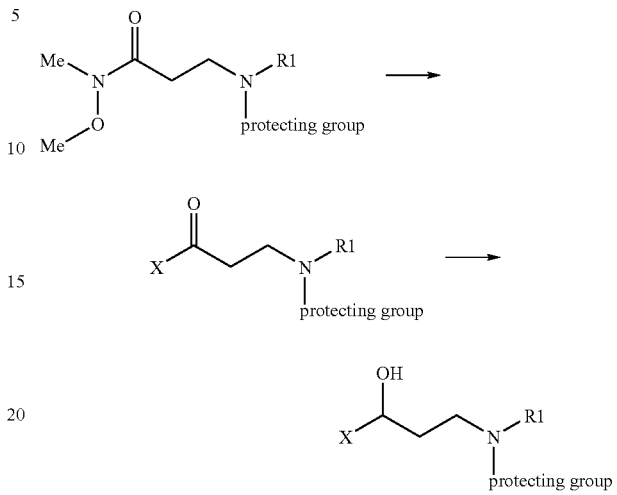

Subjecting a Weinreb amide of N-methyl β-alanine appropriately protected at the nitrogen, for example as a t-butyl carbamate (Boc) or as a benzyl amine, to an organometallic reagent like an alkyl Grignard or alkyl lithium results in the desired X-substituted ketone. The ketone can be readily reduced to the desired racemic alcohol using standard reducing agents such as sodium borohydride in a protic solvent such as lower order alkyl alcohols.

The Weinreb amides of this invention may be prepared by conventional organic chemistry techniques as exemplified below:

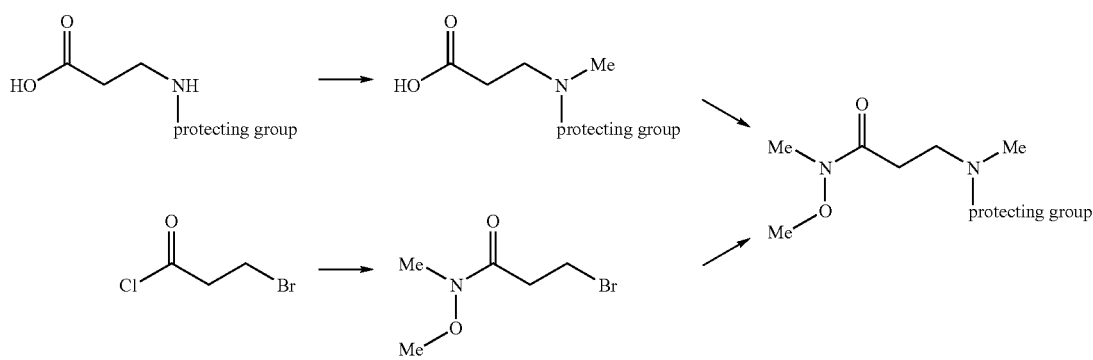

Subjecting a commercially available appropriately N-protected β-alanine to sodium hydride followed by methyl iodide results in the N-methylated derivative, which then can be converted to the Weinreb amide by reaction with N-methyl-O-methylhydroxylamine. The Weinreb amides can also be prepared by reacting a 3-bromopropanoyl chloride with N-methyl-O-methylhydroxylamine to give the Weinreb amide of 3-bromopropanoic acid, which then can be substituted with an appropriately substituted amine to give the desired Weinreb amide.

Another preferred route to 1-X, 3-aminopropanols is addition of a suitable organometallic reagent to an appropriately N-protected aminoaldehyde. Thus an appropriately protected amine can be added to a vinyl aldehyde in a Michael addition reaction to give a 3-aminoaldehyde. The aminoaldehyde can be subjected to (for example) an alkyl Grignard reagent or an alkyl lithium reagent to give the desired 1-alkylpropanol. Selection of other Grignard reagents or organolithium reagents could provide other 1-X,3-aminopropanols.

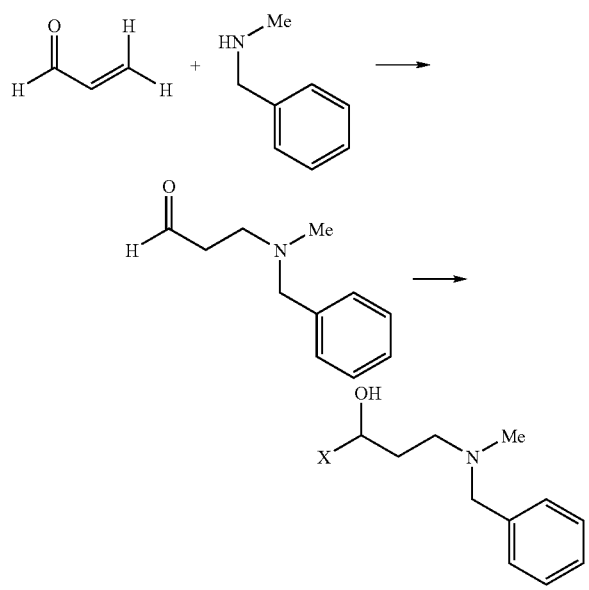

Where Z is H and X is phenyl or thienyl, the corresponding ethers and thioethers can typically be prepared generally as follows (W, X, A and Y are as defined above).

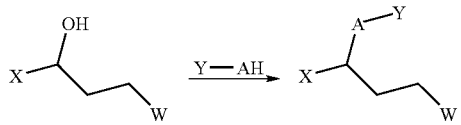

The chiral hydroxy intermediates are subjected to arylation reactions. Various arylation conditions can be used such as the Mitsunobu reaction, wherein roughly equal quantities of the heteroaryl alcohol and chloropropanol or iodopropanol are stirred at temperatures of between 0° C. and reflux in a polar non-protic solvent such as THF, with a complexing agent such as diethyl azodicarboxylate, or other derivative with a phosphine ligand such as triphenylphosphine. Alternatively 4,4-(dimethyl-1,1-dioxido-1,2,5-thiadiazolidin-2-yl)-triphenyl phosphonium in THF or toluene may be used in place of mixtures diethyl azodicarboxylate and triphenylphosphine. This type of reaction is well known and further combinations of the Mitsunobu reagents can be found in Organic Preparations and Procedures Int., 1996, 28, 2, 165 and references therein. Note however that for converting hydroxy to aryl sulfide it is preferred to react the propanol species with Y—SH, (cyanomethyl)trimethylphosphonium iodide (Tetrahedron, 2001, 57, 5451-5454) and diisopropylamine in propionitrile.

The corresponding ethers and thioethers can be readily converted to the amines by heating in a sealed vessel with the appropriate amine in a lower alkyl alcohol solvent, at temperatures between 100° C. and 150° C. for between 1 and 6 hours. To aid handling of the resulting amines their organic acid salts can typically be prepared using equimolar quantities of the propanolamines with an organic acid such as oxalic and maleic acid. The reactants are generally combined in a mutual solvent such as ethyl acetate, and the salt normally precipitates out over time and can be isolated by filtration, or by removing the solvent in vacuo, re-dissolving in purified water and freeze drying to obtain the salt.

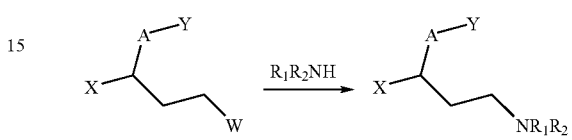

Where Z is H and X is $C_2$-$C_8$ alkyl, $C_2$-$C_8$ alkenyl, $C_3$-$C_8$ cycloalkyl or $C_4$-$C_8$ cycloalkylalkyl the corresponding ethers and thioethers can typically be prepared under arylation conditions as described above. Deprotection of the amine group provides the compounds of the invention.

The following methodology applies where Z is OH and X is phenyl, $C_2$-$C_8$ alkyl, $C_2$-$C_8$ alkenyl, $C_3$-$C_8$ cycloalkyl or $C_4$-$C_8$ cycloalkylalkyl.

The "anti" chain hydroxylated propanamines may be prepared using the methodology outlined below. Although X is shown as optionally substituted phenyl in the reaction schemes below, the same methodology could be applied for other identities of X (except thienyl).

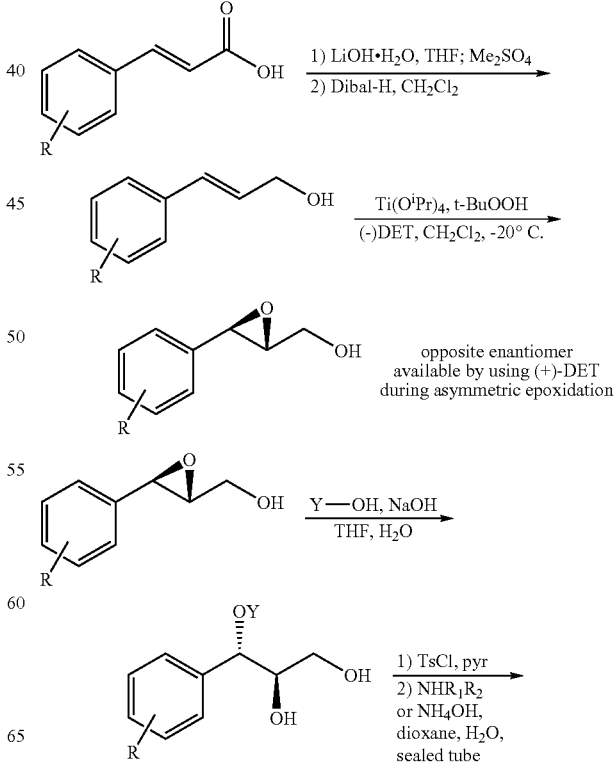

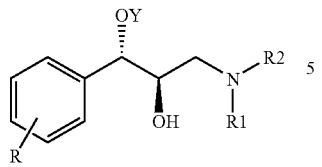

The "syn" chain hydroxylated propanamines may be prepared using the method outlined below (conversion of (I) to (II) is further described in *Tetrahedron Let.* 1986, 41, 4987). Although X is shown as phenyl in the reaction schemes below, the same methodology could be applied for other identities of X (except thienyl).

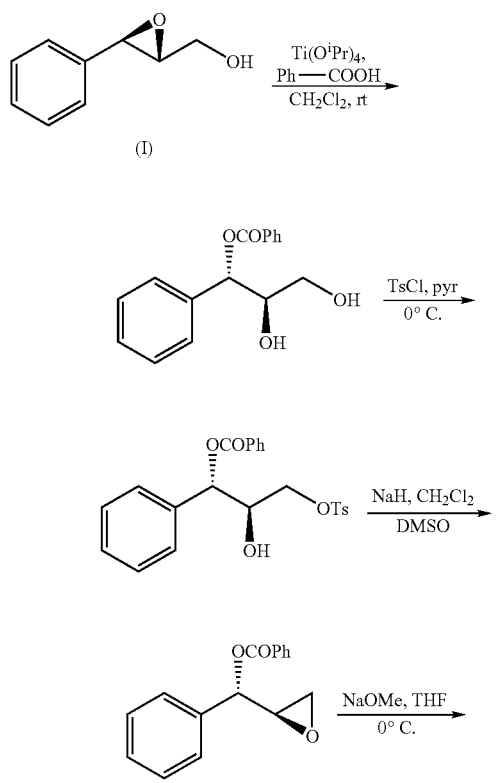

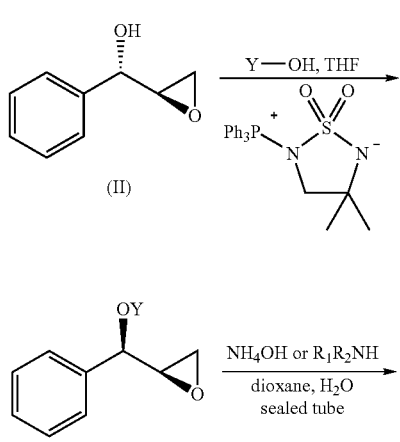

Alternatively, the "syn" chain hydroxylated propanamines, may be prepared using the method outlined below.

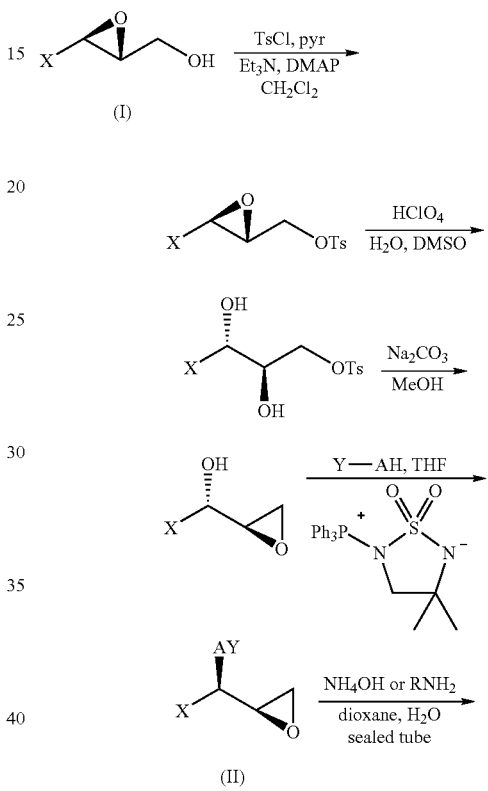

Alternatively, the "syn" and "anti" chain hydroxylated propanamines may be prepared using the intermediates shown below.

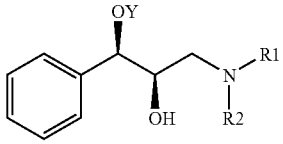

The same chemical transformations may be applied to each intermediate to obtain each of the four stereochemically distinct final products. For example:

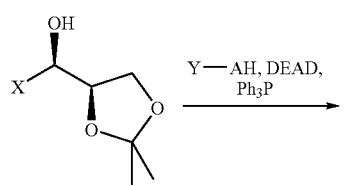

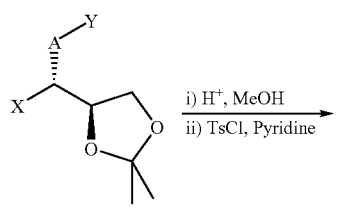

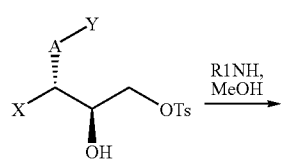

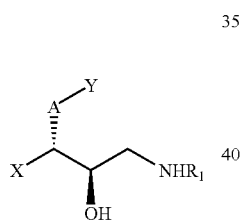

Starting from the other three intermediates, the same chemistry may be used to obtain the other three final products, i.e.

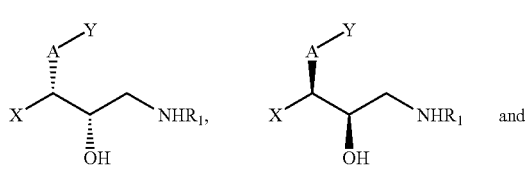

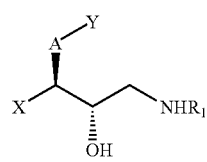

The four intermediates may be synthesized by two different routes. The first route is shown below:

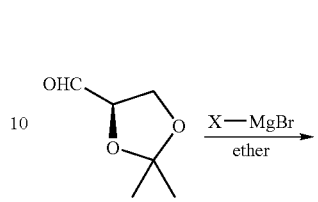

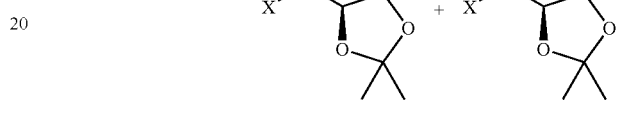

Separation of diastereoisomers

The other two intermediates may be obtained using the same chemistry but starting with the compound:

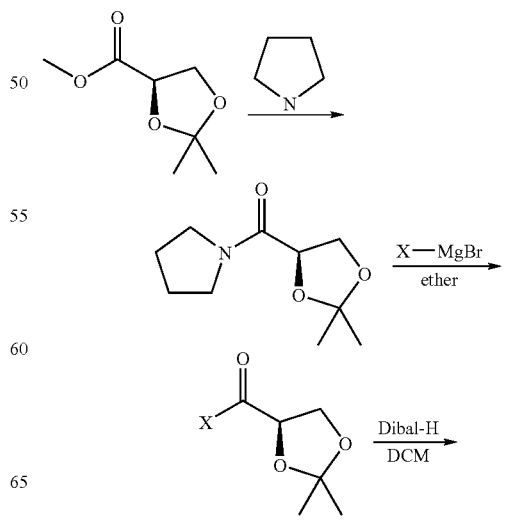

The second route is shown below:

-continued

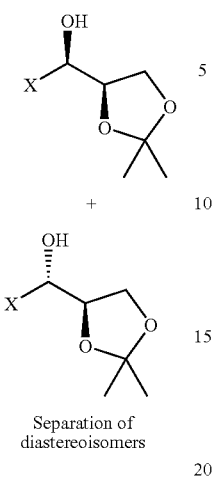

Separation of diastereoisomers

The other two intermediates may be obtained using the same chemistry but starting with the compound:

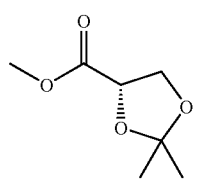

4,4-(dimethyl-1,1-dioxido-1,2,5-thiadiazolidine-2-yl)-triphenyl phosphonium is prepared according to J. Org. Chem. 1994, 59, 2289.

The following methodology applies where Z is F and X is phenyl, $C_2$-$C_8$ alkyl, $C_2$-$C_8$ alkenyl, $C_3$-$C_8$ cycloalkyl or $C_4$-$C_8$ cycloalkylalkyl.

The "syn" chain fluorinated propanamines may be prepared using the method outlined below. Although X is shown as optionally substituted phenyl in the reaction schemes below, the same methodology could be applied for other identities of X (except thienyl).

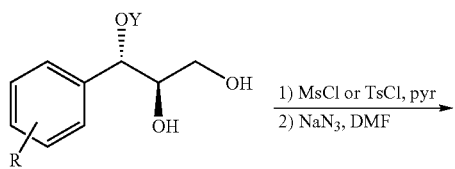

Prepared as outlined for "anti" hydroxylated propanamines

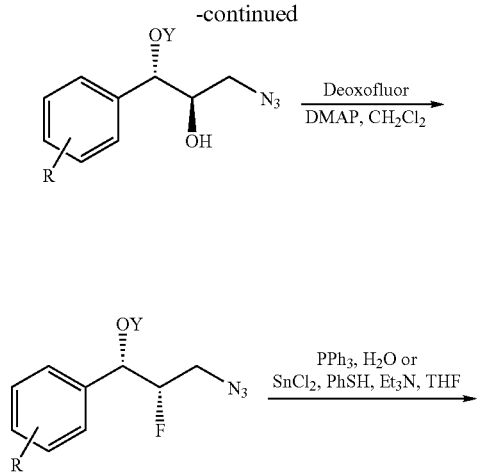

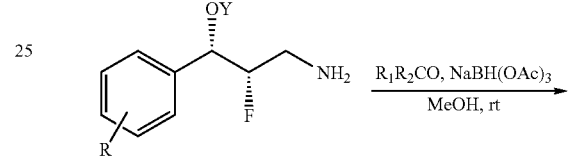

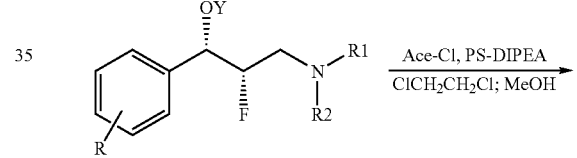

The "anti" chain fluorinated propanamines may be prepared using the method outlined below. Although X is shown as optionally substituted phenyl in the reaction schemes below, the same methodology could be applied for other identities of X (except thienyl).

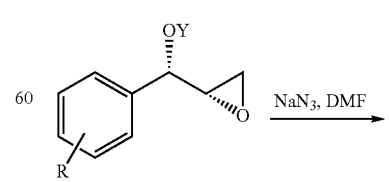

prepared as outlined for the "syn" hydroxylated propanamines

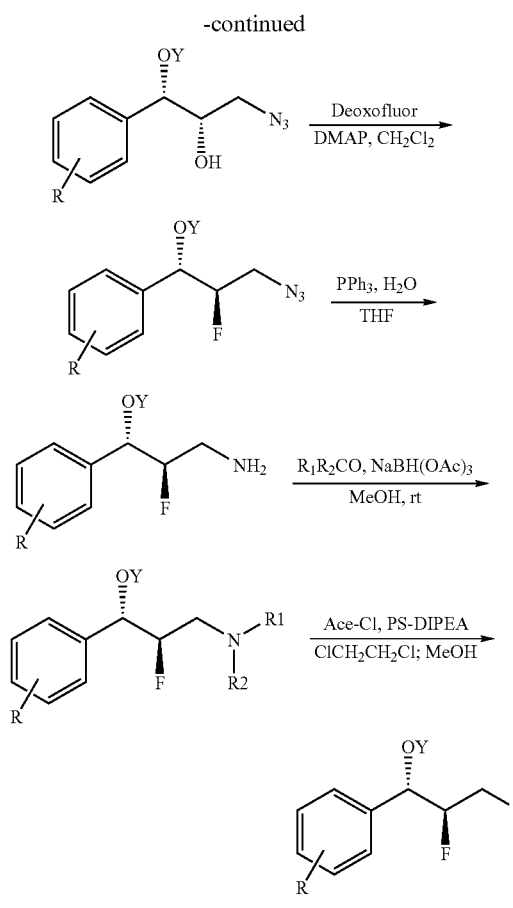

When X is thienyl, the hydroxylated propanamines may be prepared using the methodology outlined below.

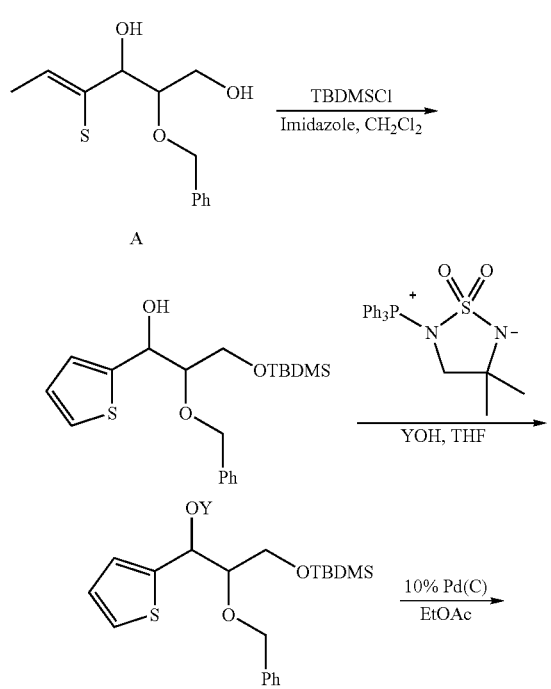

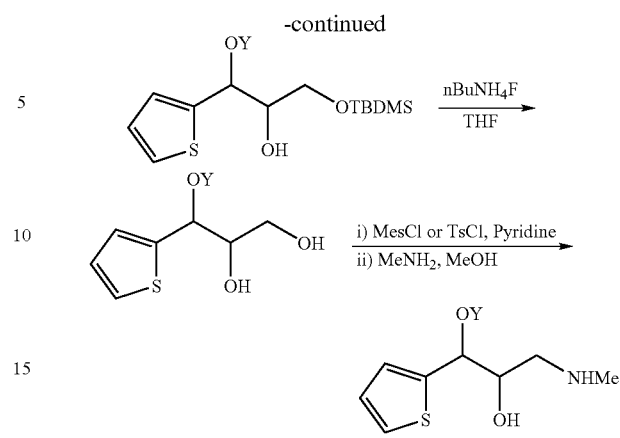

The synthesis of A is described in the reference S. Kobayashi, I. Hachiya, M. Yasuda; Tetrahedron Letters, 1996, 37(31), 5569-5572. The mixture of stereoisomers obtained by this route is firstly separated by achiral chromatography to give a mixture of chiral diasteroisomers, then by chiral chromatography to separate the mixture of chiral diasteroisomeric isomers into individual chiral final products.

When X is thienyl, the fluorinated propanamines may be prepared using the methodology outlined below.

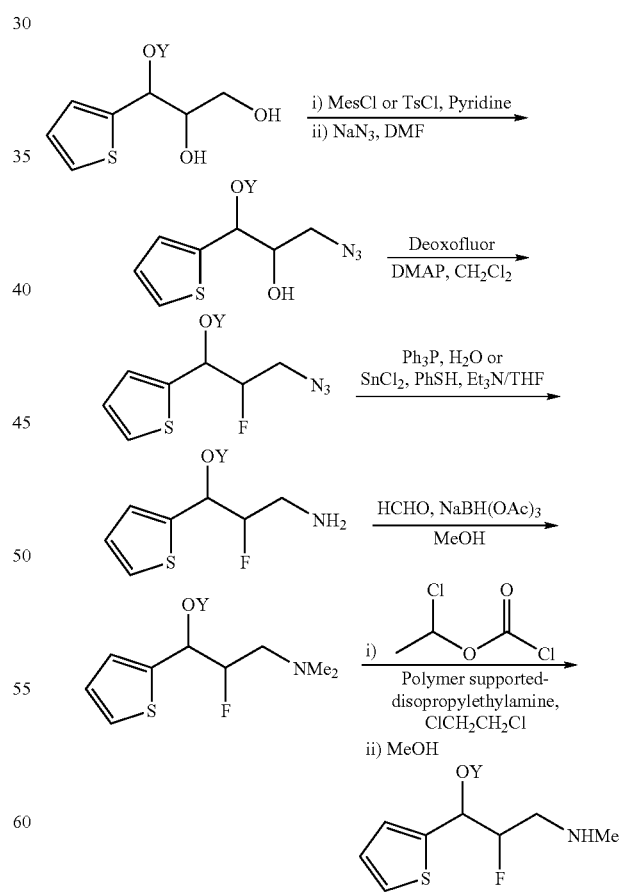

The starting material is synthesized as shown in the previous scheme. The mixture of stereoisomers obtained by this route is firstly separated by achiral chromatography to give a mixture of chiral diasteroisomers, then by chiral chromatography to separate the mixture of chiral diasteroisomeric isomers into individual chiral final products.

Use of Y—SH in place of Y—OH in the above methodologies where Z is OH or F provides compounds wherein A is S. Note however that for converting hydroxy to aryl sulfide it is preferred to react the propanol species with Y—SH, (cyanomethyl)trimethylphosphonium iodide (Tetrahedron, 2001, 57, 5451-5454) and diisopropylamine in propionitrile.

Compounds of formula I where $R_1$=methyl and $R_2$=H may be prepared by solid phase synthesis by the route shown below.

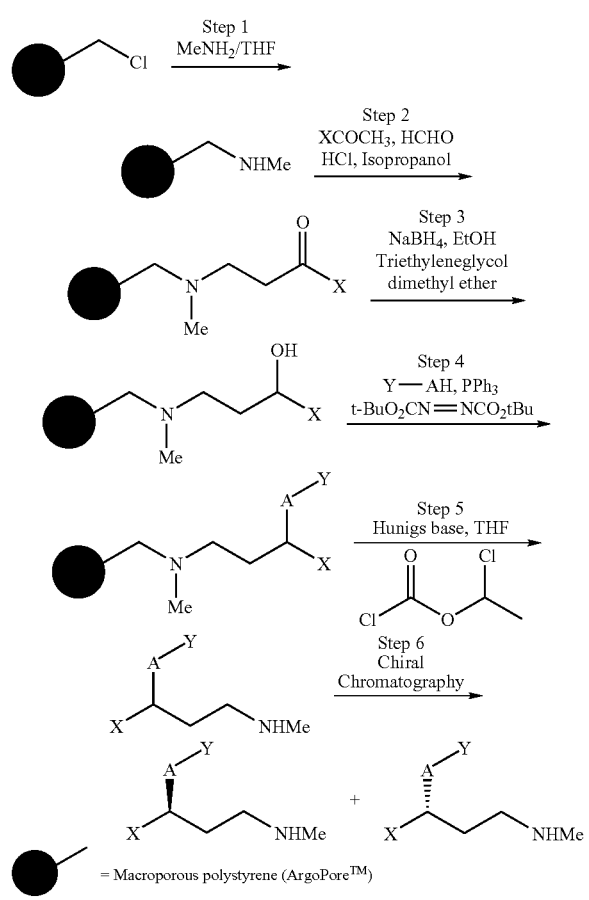

The sequence is preferably performed on a macroporous polystyrene resin, e.g. ArgoPore™. Thus ArgoPore-Cl is converted with methylamine in methanol to a secondary amine bound to the resin. A Mannich type reaction is then performed on the resin bound amine with aqueous formaldehyde, hydrochloric acid a substituted acetophenone and isopropanol. The resultant aminoketone is then reduced with sodium borohydride in ethanol/triethyleneglycol dimethyl ether to give the amino alcohol. This is then subjected to a Mitsunobu reaction using di-t-butylazodicarboxylate, triphenyl phosphine and a heteroaryl alcohol/thiol (Y-AH) to give a resin bound heteroaryl aminothioether. Removal of the aminoether from the resin is effected with 1-chloroethyl chloroformate and Hunigs base in THF. Finally resolution of the enantiomers is achieved using chiral chromatography.

The following Examples further illustrate the compounds of the present invention and methods for their synthesis.

In the following section, there is described the synthesis of precursors and common intermediates for the compounds of the present invention.

(S)-(−)-3-Iodo-1-phenyl-1-proyanol

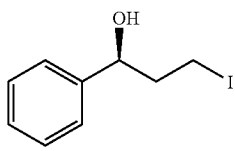

To a solution of (S)-(−)-3-chloro-1-phenyl-1-propanol (5 g, 29.3 mmol) in acetone (50 mL) was added sodium iodide (4.83 g, 32.2 mmol). The resulting solution was heated at reflux for 16 h. The solution was cooled, filtered and concentrated in vacuo. The residue was purified by flash chromatography eluting silica gel with hexane: ethyl acetate [100:0 to 3:1] to yield the iodo compound (7.44 g, 97%); $\delta_H$ (300 MHz, CDCl$_3$) 7.36 (5H, m, Ar), 4.83 (1H, m, O—CH), 3.34-3.15 (2H, m, CH$_2$), 2.28-2.15 (2H, m, CH$_2$).

(R)-(+)-3-Iodo-1-phenyl-1-propanol

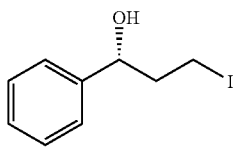

To a solution of (R)-(+)-3-chloro-1-phenyl-1-propanol (5 g, 29.3 mmol) in acetone (50 mL) was added sodium iodide (4.83 g, 32.2 mmol). The resulting solution was heated at reflux for 16 h. The solution was cooled, filtered and concentrated in vacuo. The residue was purified by flash chromatography eluting silica gel with hexane: ethyl acetate [100:0 to 3:1] to yield the title compound as a white solid (7.51 g, 98%); $\delta_H$ (300 MHz, CDCl$_3$) 7.36 (5H, m, Ar), 4.83 (1H, m, O—CH), 3.34-3.15 (2H, m, CH$_2$), 2.28-2.15 (2H, m, CH$_2$).

(1R)-3-Chloro-1-(2-thienyl)-1-propanol a) 3-Chloro-1-(2-thienyl)-1-propanone

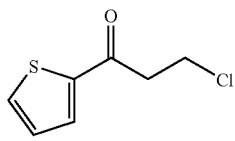

Chloropropionyl chloride (12 mL, 130 mmol) in dry dichloromethane (50 mL) was added dropwise at −5° C. to a stirred suspension of aluminium chloride (18.8 g, 141 mmol) in dry dichloromethane (100 mL). The resulting suspension was allowed to stir at −5° C. for 10 mins before a solution of thiophene (10 g, 118 mmol) in dry dichloromethane (50 mL) was added dropwise. The resulting orange solution was stirred at −5° C. for 1 hr before being carefully dropped onto crushed ice (200 g). The organic phase was separated and dried (MgSO$_4$), the solvent was then passed through a pad of celite/charcoal to remove any colour. Removal of the solvent in vacuo resulted in the title compound as a colourless oil (20 g, 100%); δ$_H$ (300 MHz, CDCl$_3$) 7.75 (1H, d, Ar), 7.68 (1H, d, Ar), 7.15 (1H, m, Ar), 3.90 (2H, t, J=7 Hz, CH$_2$), 3.38 (2H, t, J=7 Hz, CH$_2$).

b) (1R)-3-Chloro-1-(2-thienyl)-1-propanol

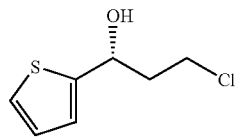

Borane dimethylsulfide complex (2.75 mL, 28.6 mmol) was added at room temperature to a stirred solution of (S)-2-methyl-CBS-oxazaborolidine (2.87 mL, 1M) in dry TXF (50 mL). The resulting solution was stirred at room temperature to 10 mins before a solution of 3-chloro-1-(2-thienyl)-1-propanone (2.5 g, 14.3 mmol) in dry THF (100 mL) was added dropwise over 1 hr. After complete addition the resulting solution was stirred at room temperature for a further 1 hr before the solvent was removed in vacuo. The residue was taken up in ether (200 mL) and washed with NH$_4$Cl (sat, 100 mL). The organic phase was dried (MgSO$_4$) and concentrated in vacuo. The residue was purified by flash chromatography eluting silica gel with hexane:ether [7:3] to yield a colourless oil (2.1 g, 84%); Optical purity determined by capillary electrophoresis to be 83% ee; δ$_H$ (300 MHz, CDCl$_3$) 7.25 (1H, d, Ar), 7.08-6.9 (2H, m, Ar), 5.28-5.20 (1H, m, CHO), 3.80-3.52 (2H, m, CH$_2$), 2.35-2.12 (2H, m, CH$_2$).

3-[Benzyl(methyl)amino]-1-phenyl-1-propanol

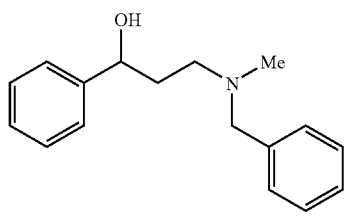

A solution of 3-chloro-1-phenylpropan-1-ol (2 g, 11.7 mmol), N-methylbenzylamine (2.12 g, 17.5 mmol), potassium iodide (2.6 g, 22 mmol), and potassium carbonate (3.2 g, 23.4 mmol) in dimethylformamide (120 mL) was stirred at 90° C. in a reacti-vial for 16 h. After this time the reaction was allowed to cool to room temperature. The reaction mixture was purified by an SCX-2 column eluting with Methanol followed by ammonia:methanol solution (7 N). The organics were then evaporated and the compound taken directly onto the next step without any further purification. (M$^+$H+1 [256]);

δ$_H$ (300 MHz, CDCl$_3$) 7.2-7.4 (10H, m, Ar), 4.9 (1H, t, CH—OH), 3.55 (1H, d, CH$_2$-Ph), 3.45 (1H, d, CH$_2$—PH), 2.8-3 (1H, m, CH$_2$), 2.55-2.65 (1H, m, CH$_2$), 2.25 (3H, s, CH$_3$), 1.89-1.9 (2H, m, CH$_2$), 1.6 (1H, brs, OH).

3-(Benzyl-methyl-amino)-N-methoxy-N-methyl-propionamide

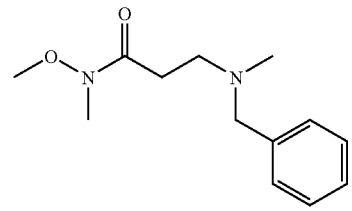

Add potassium carbonate (63.50 g, 459 mmol) to a stirred solution of N-benzylmethylamine (14.8 mL, 115 mmol), 3-bromo-N-methoxy-N-methyl-propionamide (22.47 g, 115 mmol, prepared according to Jacobi, P. A.; Blum, C. A.; DeSimone, R. W.; Udodong, U. E. S. *J. Am. Chem. Soc.* 1991, 113, 5384-5392), and anhydrous acetonitrile (460 mL). Heat the reaction to reflux under nitrogen for 3 hours. Cool the reaction to room temperature and filter the reaction through Celite®. Wash the Celite® with ethyl acetate and concentrate on a rotary evaporator to give the crude product. Purify the crude product by flash chromatography on silica gel eluting with 0.5% concentrated ammonium hydroxide/5% ethanol/chloroform to yield 22.31 g (82%) of 3-(benzyl-methyl-amino)-N-methoxy-N-methyl-propionamide: mass spectrum (ion spray) m/z=237.1(M+1); $^1$H NMR (CDCl$_3$) δ 7.31-7.21 (m, 5H), 3.65 (s, 3H), 3.53 (s, 2H), 3.17 (s, 3H), 2.80-2.76 (m, 2H), 2.67-2.63 (m, 2H), 2.23 (s, 3H).

1-(Benzyl-methyl-amino)-heptan-3-one

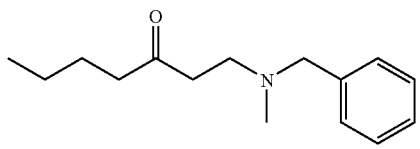

Add butyllithium (12.3 ml (1.6 M solution in hexane), 19.6 mmol) to a stirred solution of 3-(benzyl-methyl-amino)-N-methoxy-N-methyl-propionamide and anhydrous tetrahydrofuran (70 ml) at −40° C. under N$_2$. Stir for 1 hr at −40° C. Quench the reaction with saturated ammonium chloride (25 ml), allow the reaction to reach room temperature and add saturated sodium bicarbonate. Extract with ethyl acetate, wash with brine and dry over sodium sulfate. Filter off and concentrate to give the crude product. Purify the compound by flash chromatography, eluting with 2% ethanol/0.2% ammonium hydroxide/chloroform to yield 2.41 g (81%) of 1-(benzyl-methyl-amino)-heptan-3-one: mass spectrum (ion spray) m/z=234 (M+1); $^1$H NMR (CDCl$_3$) δ 7.31-7.24 (m, 5H), 3.5 (s, 2H), 2.74-2.7 (m, 2H), 2.64-2.60 (m, 2H), 2.41 (t, 2H), 2.19 (s, 3), 1.59-1.51 (m, 2H), 1.35-1.28 (m, 2H), 0.91 (t, 3H).

1-(Benzyl-methyl-amino)-hexan-3-one

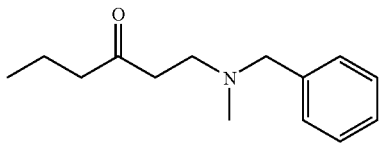

Using a method similar to that for 1-Benzyl-methyl-amino)-heptan-3-one, propylmagnesium chloride (2 M solution in diethyl ether) affords the title compound: mass spectrum (ion spray) m/z=220 (M+1): 1H NMR (CDCl₃) δ 7.35-7.24 (m, 5H), 3.51 (s, 2H), 2.74-2.69 (m, 2H), 2.66-2.61 (m, 2H), 2.39 (t, 2H), 2.20 (s, 3H), 1.67-1.57 (m, 2H), 0.92 (t, 3H),

(4-Cyclohexyl-3-oxo-butyl)-methyl-carbamic acid tert-butyl ester

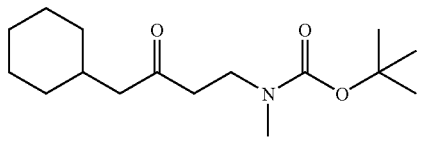

Add dropwise bromomethylcyclohexane (16.96 mL, 0.121 mol) to a stirred warm solution of magnesium (granulae, 3.02 g, 0.124 mol), a crystal of iodine and tetrahydrofuran (130 mL). Heat the mixture to reflux for one hour. Add the Grignard reagent (30 mL) to a stirred mixture of [2-(methoxy-methyl-carbamoyl)-ethyl]-methyl-carbamic acid tert-butyl ester (3.0 g, 12.0 mmol, prepared according to Blaney, P.; Grigg, R.; Rankovic, Z.; Thornton-Pett, M.; Xu, J. *Tetrahedron* 2002, 1719-1737) and tetrahydrofuran (120 mL) kept at 0° C. under N₂. Stir the mixture for one h at 0° C. and for 2 h at room temperature. Add more of the Grignard reagent (40 mL) and stir for another hour at room temperature. Add saturated aqueous ammonium chloride and separated the layers. Extract the water layer with diethyl ether (×3). Dry the combined organic layers, filter and concentrate. Purify the crude residue by flash column chromatography, eluting with ethyl acetate/hexane (1:9) to yield 1.0 g of the title compound. ¹H NMR (CDCl₃) δ 3.46-3.40 (m, 2H), 2.85 (s, 3H), 2.68-2.60 (m, 2H), 2.29 (d, 2H), 1.87-1.60 (m, 6H), 1.46 (s, 9H), 1.33-1.07 (m, 3H), 0.99-0.86 (m, 2H).

1-(Benzyl-methyl-amino)-heptan-3-ol

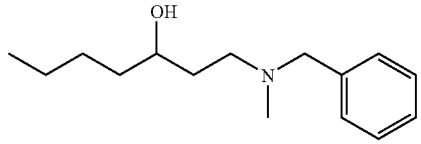

Add sodium borohydride (1.29 g, 34.1 mmol) to a stirred solution of 1-(benzyl-methyl-amino)-heptan-3-one (2.41 g, 10 mmol) and methanol (45 ml) at 0° C. under N₂. Stir the reaction for 1 hr at 0° C. Quench the reaction with water at 0° C. and concentrate under reduced pressure. Dissolve the residue in ethyl acetate, wash with brine and dry over sodium sulfate. Filter off and concentrate to give the crude compound. Purify the compound by flash chromatography, eluting with 5% ethanol/0.5% ammonium hydroxide/chloroform to yield 2.22 g (91%) of 1-(benzyl-methyl-amino)-heptan-3-ol: mass spectrum (ion spray) m/z=236 (M+1); ¹H NMR (CDCl₃) δ 7.34-7.23 (m, 5H), 3.76-3.72 (m, 1H), 3.53 (dd, 2H), 2.80-2.73 (m, 1H), 2.59-2.53 (m, 1H), 2.21 (s, 1H), 1.68-1.62 (m, 1H), 1.57-1.29 (m, 7H), 0.91 (t, 3H).

1-(Benzyl-methyl-amino)-hexan-3-ol

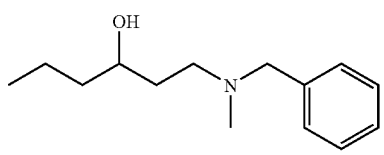

Using a method similar to that for 1-(Benzyl-methyl-amino)-heptan-3-ol, 1-(benzyl-methyl-amino)-hexan-3-one affords the title compound: mass spectrum (ion spray) m/z 222 (M+1); ¹H NMR (CDCl₃) δ 7.34-7.24 (m, 5H), 3.79-3.73 (m, 1H), 3.55 (dd, 2H), 2.81-2.74 (m, 1H), 2.59-2.55 (m, 1H), 2.22 (s, 3H), 1.72-1.62 (m, 1H), 1.56-1.31 (m, 5H), 0.93 (t, 3H).

(4-Cyclohexyl-3-hydroxy-butyl)-methyl-carbamic acid tert-butyl ester

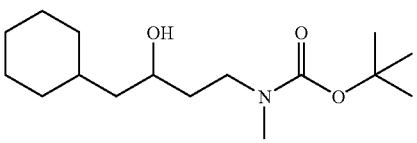

Using a method similar to that for 1-(Benzyl-methyl-amino)-heptan-3-ol, (4-cyclohexyl-3-oxo-butyl)-methyl-carbamic acid tert-butyl ester affords the title compound: ¹H NMR (CDCl₃) δ 3.90-3.80 (m, 1H), 3.62-3.52 (m, 1H), 2.88-2.96 (m, 1H), 2.83 (3H), 1.80-1.60 (m, 6H), 1.56-1.32 (m, 3H), 1.47 (s, 9H), 1.31-1.08 (m, 4H), 0.98-0.77 (m, 2H),

1-(Benzyl-methyl-amino)-5-methyl-hexan-3-ol

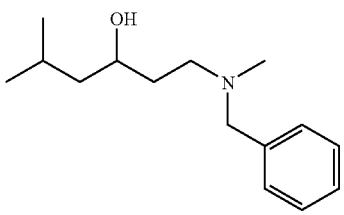

Add N-benzylmethylamine (1.50 mL, 11.6 mmol) to a stirred solution of 1,8-diazabicyclo[5.4.0]undec-7-ene (0.0175 mL, 0.117 mmol) and anhydrous tetrahydrofuran (10 mL). Cool the solution to −15° C. under nitrogen. Add acrolein (0.78 mL, 11.7 mmol) slowly and stir for 30 minutes at −15° C. Cool the reaction to −78° C. Add isobutylmagnesium chloride (11.0 mL, 2.0 M solution in diethyl ether, 22.0 mmol) and stir for 1 hour at −78° C. Quench the reaction with water at −78° C. and then pour the reaction into 100 mL of 1N sodium hydroxide/saturated sodium bicarbonate (1:1). Extract with ethyl acetate (3×100 mL), wash the ethyl acetate with brine (100 mL), and dry the ethyl acetate over sodium sulfate. Filter off the sodium sulfate and concentrate on a rotary evaporator to give the crude product. Purify the crude product by flash chromatography on silica gel eluting with 0.3% concentrated ammonium hydroxide/3% ethanol/chloroform to yield 1.0010 g (37%) of 1-(benzyl-methyl-amino)-5-methyl-hexan-3-ol: mass spectrum (ion spray) m/z=236.2 (M+1); $^1$H NMR (CDC$_3$) δ 7.34-7.23 (m, 5H), 6.08 (br s, 1H), 3.86-3.80 (m, 1H), 3.62 (d, 1H), 3.43 (d, 1H), 2.79-2.73 (m, 1H), 2.58-2.53 (m, 1H), 2.21 (s, 3H), 1.83-1.40 (m, 4H), 1.16-1.09 (m, 1H), 0.91-0.89 (m, 6H).

1-(Benzyl-methyl-amino)-4-methyl-pentan-3-ol

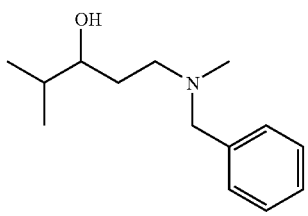

Using a method similar to that for 1-(Benzyl-methyl-amino)-5-methyl-hexan-3-ol, isopropylmagnesium chloride affords the title compound: mass spectrum (ion spray) m/z=222.1(M+1); $^1$H NMR (CDCl$_3$) δ 7.34-7.23 (m, 5H), 6.21 (br s, 1H), 3.63 (d, 1H), 3.51-3.47 (m, 1H), 3.42 (d, 1H), 2.81-2.74 (m, 1H), 2.59-2.54 (m, 1H), 2.19 (s, 3H), 1.72-1.47 (m, 3H), 0.95 (d, 3H), 0.89 (d, 3H).

Isoquinolin-4-ol

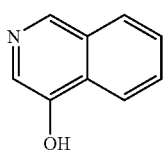

The title compound was prepared as described in *Tetrahedron*, 1963, 19, 827-832.

Isoquinolin-6-ol a) 6-Methoxy-isoquinoline

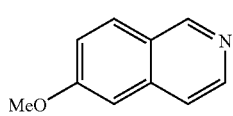

The title compound was prepared as described in *Synth. Commun.*, 1999, 29, 1617-1625.

b) Isoquinolin-6-ol

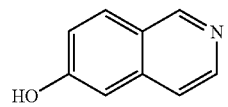

Heat a mixture of 6-methoxy-isoquinoline (2.1 g, 13.2 mmol) and pyridine hydrochloride (30 g) in a heavy walled screw cap sealed tube at 160° C. overnight. Cool to room temperature, add water and concentrated ammonium hydroxide to bring the pH of the mixture to 10-11, extract with ethyl acetate (4 times), wash the combined organic extracts with water (4 times), and concentrate under reduced pressure. Purification by medium pressure liquid chromatography eluting with 0-3% of 2N NH$_3$/MeOH in dichloromethane afford the title compound (520 mg, 27%): δ$_H$ (DMSO-d6, 400 MHz): 7.09 (s, 1H), 7.19 (dd, 1H, J=9, 2 Hz), 7.56 (d, 1H, J=6 Hz), 7.94 (d, 1H, J=9 Hz), 8.29 (d, 1H, J=6 Hz), 9.05 (s, 1H), 10.36 (s, 1H).

[1,7]Naphthyridin-5-ol

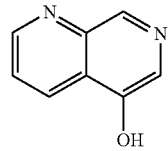

The title compound was prepared as described in *Liebigs Annalen Der Chemie*, 1979, 443-445.

5-Hydroxyisoquinoline

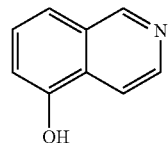

The title compound is commercially available and was purchased from the Aldrich Chemical Company.

5-Quinolinol

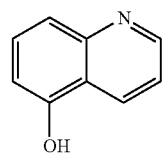

The title compound is commercially available and was purchased from the Aldrich Chemical Company.

Benzo[d]isothiazol-4-ol a) 4-Methoxy-benzo[d]isothiazole

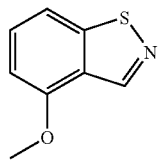

To a solution of 2-fluoro-6-methoxybenzaldehyde (2.0 g, 13.0 mmol) in 2-methoxyethanol (10 mL) in a sealed tube was added sulfur (416 mg, 13.0 mmol) and aqueous ammonium hydroxide (10 mL). The solution was heated to 160 degC. for 18 h and was then cooled to rt. The reaction was partitioned between dichloromethane and water. The organic layer was separated and the aqueous layer was extracted with 2×50 mL dichloromethane. The combined organic phases were dried (MgSO$_4$) and concentrated in vacuo. The residue was purified by flash chromatography eluting silica gel with EtOAc:hexane [0:100 to 4:6] to yield the title compound as an oil (1.51 g, 70%); Mass spectrum (ion spray): m/z=165.9 (m+1).

b) Benzo[d]isothiazol-4-ol

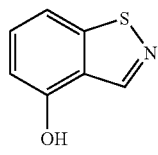

To a sealed tube was added 4-methoxy-benzo[d]isothiazole (760 mg, 4.60 mmol) and pyridine hydrochloride (5.5 g, 48 mmol). The reaction was heated to 150° C. for 18 h and was then cooled to rt. The mixture was partitioned between dichloromethane and water. The organic phase was separated and the aqueous layer was extracted with 2×30 mL dichloromethane. The combined organic phases were dried (MgSO$_4$) and concentrated in vacuo. The residue was purified by flash chromatography eluting silica gel with EtOAc:hexane [0:100 to 3:7] to yield the title compound as a solid (223 mg, 32%); Mass spectrum (ion spray): m/z=151.9 (m+1).

7-methyl-benzo[d]isothiazol-4-ol a) 7-Bromo-4-methoxy-benzo[d]isothiazole

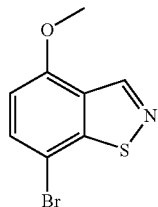

To a solution of 4-methoxy-benzo[d]isothiazole (prepared as described above) (1.0 g, 6.05 mmol) in carbon tetrachloride (20 mL) at 0° C. was added bromine (310 μL, 6.05 mmol) in carbon tetrachloride (10 mL). The reaction was allowed to stir at 0° C. for 3 h and was then warmed to rt. Saturated aqueous NaHCO$_3$ and dichloromethane were added and the organic phase was separated. The aqueous phase was extracted with 2×20 mL dichloromethane. The combined organic phases were dried (MgSO$_4$) and concentrated in vacuo. The residue was purified by flash chromatography eluting silica gel with FtOAc:hexane [0:100 to 1:20] to yield the title compound (980 mg, 66%): δ$_H$ (300 MHz, CDCl$_3$): 9.09 (1H, s), 7.52 (1H, d, J=8.1 Hz), 6.67 (1H, d, J=8.4 Hz), 4.00 (3H, s).

b) 7-methyl-benzo[d]isothiazol-4-ol

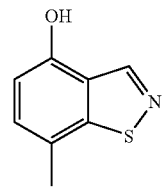

A solution of 7-4-methoxy-benzo[d]isothiazole (460 mg, 1.88 mmol), K$_2$CO$_3$ (780 mg, 5.64 mmol), and Pd(PPh$_3$)$_4$ (217 mg, 0.188 mmol) in 1,4-dioxane (5 mL) was added trimethylboroxine (290 μL, 2.07 mmol) and the solution was heated to 110° C. for 18 h. The reaction was cooled to rt and diluted with water and dichloromethane. The organic phase was separated and the aqueous phase was extracted with 2×30 mL dichloromethane. The combined organic phases were dried (MgSO$_4$) and concentrated in vacuo. The residue was purified by flash chromatography eluting silica gel with EtOAc:hexane [0:100 to 1:10] to yield 4-methoxy-7-methyl-benzo[d]isothiazole (88 mg, 26%). A method similar to that described for the preparation of benzo[d]isothiazol-4-ol (above) using 4-methoxy-7-methyl-benzo[d]isothiazole (88 mg, 0.491 mmol) and pyridine hydrochloride (567 mg, 5 mol) gave the title compound (30 mg, 37%): δ$_H$ (300 MHz, CDCl$_3$): 8.99 (1H, s), 7.15 (1H, d, J=7.5 Hz), 6.70 (1H, d, J=7.5 Hz), 2.45 (3H, s).

Benzo[d]isothiazol-7-ol a) 2-Fluoro-3,N-dimethoxy-N-methyl-benzamide

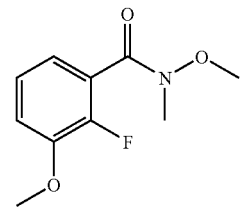

To a solution of 2-fluoro-3-methoxy-benzoic acid (5.0 g, 29.4 mmol) and PyBOP (13.7 g, 29.4 mmol) in 7:1 CH$_2$Cl$_2$:THF was added triethylamine (4.10 mL, 29.4 mmol) over a 10 min period. N,O-Dimethylhydroxylamine hydrochloride (2.87 g, 29.4 mL) was then added and the reaction was allowed to stir at rt for 3 h. The reaction was then partitioned between dichloromethane and water. The organic phase was separated and the aqueous phase was extracted with 2×100 mL dichloromethane. The combined organic phases were dried (MgSO$_4$) and concentrated in vacuo. The residue was taken up in ethyl acetate and was washed successively with 1N HCl, saturated aqueous NaHCO$_3$, and brine. The organic phase was again dried (MgSO$_4$) and concentrated in vacuo to yield the title compound (2.30 g, 37%).

b) 2-Fluoro-3-methoxy-benzaldehyde

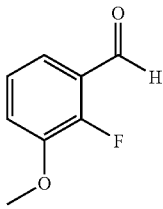

To a solution of 2-fluoro-3,N-dimethoxy-N-methyl-benzamide (2.30 g, 10.8 mmol) in THF (20 mL) at −78° C. was added 1M DEBAL-H in toluene.(12 mL, 12 mmol). The reaction stirred at −78° C. for 3 h and then the remaining 1M DIDAL-H in toluene (4.2 mL, 4.2 mmol) was added to the reaction. The reaction was allowed to stir at −78° C. for 30 min and was then warmed to rt. The reaction was quenched slowly with saturated aqueous NH$_4$Cl. The organic phase was separated and the aqueous phase was extracted with 2×50 mL ethyl acetate. The combined organic phases were washed successively with 1N HCl and brine. The organic phase was dried (MgSO$_4$) and concentrated in vacuo. The residue was purified by flash chromatography eluting silica gel with EtOAc:hexane [0:100 to 1:1] to yield the title compound (1.41 g, 85%): δ$_H$ (300 MHz, CDCl$_3$): 10.38 (1H, s), 7.43-7.40 (1H, m), 7.24-7.15 (2H, m), 3.95 (3H, s).

c) 7-methoxy-benzo[d]isothiazole

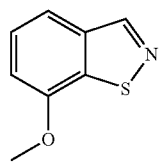

A method similar to 4-methoxy-benzo[d]isothiazole using 2-fluoro-3-methoxy-benzaldehyde (410 mg, 2.66 mmol), sulfur (85 mg, 2.66 mmol), NH$_4$OH (5 mL), and 2-methoxyethanol (5 mL) gave the title compound (60 mg, 14%); Mass spectrum (ion-spray): m/z=165.8 (m+1).

d) Benzo[d]isothiazol-7-ol

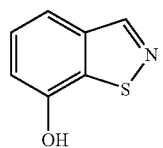

A method similar to that used in the preparation of benzo[d]isothiazol-4-ol using 7-methoxy-benzo[d]isothiazole (60 mg, 0.363 mmol) and pyridine hydrochloride (500 mg, 4.33 mmol) gave the title compound (26 mg, 47%); Mass spectrum (ion-spray): m/z=151.9 (m+1).

4-Hydroxy-benzothiazole a) 4-Methoxy-benzothiazole

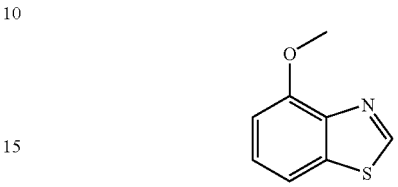

2-Amino-4-methoxy-benzothiazole (1.00 g, 5.54 mmol) was added to a stirred solution of polyphosphoric acid (85%, 40 ml) at 60° C. The resulting mixture was stirred at 60° C. until all the benzothiazole had dissolved. The resulting solution was then cooled to −10° C. and a solution of sodium nitrite (2.3 g, 33.3 mmol) in water (5 ml) was added so as to keep the internal temperature below −4° C. After complete addition the resulting solution was added to a solution of hypophosphoric acid (50%, 15 ml) at 0° C. After the evolution of gas had ceased the mixture was diluted with water and basified with NaHCO$_3$ (sat). The aqueous solution was extracted with CHCl$_3$ (3×200 ml) with the combined organic extracts dried (MgSO$_4$) and the solvent removed in vacuo. The resulting solid was recrystallised from EtOH:H$_2$O to give an orange solid (300 mg).

The liquor was concentrated and purified by flash chromatography eluting silica gel with hexane:EtOAc [4:1] to hexane:EtOAc [1:1] to give a further 210 mg of product. R$_f$=0.38 in hexane:ether [1:1]; δ$_H$ (300 MHz, CDCl$_3$) 8.91 (1H, s, CH), 7.53 (1H, d, Ar), 7.39 (1H, t, Ar), 6.93 (1H, d, Ar), 4.07 (3H, s, OCH$_3$).

b) 4-Hydroxy-benzothiazole

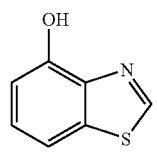

Boron tribromide (3.09 ml, 1M solution in DCM, 3.09 mmol) was added dropwise at 0° C. to a stirred solution of 4-methoxy-benzothiazole (510 mg, 3.09 mmol) in dry DCM (30 ml). The resulting solution was warmed to 40° C. and allowed to stir overnight. The resulting solution was concentrated in vacuo and diluted with water and HCl (2N). The aqueous phase was neutralised to pH ~7 with NaHCO$_3$ and the solution extracted with EtOAc (3×100 ml) and the combined organic extracts dried (MgSO$_4$) and the solvent removed in vacuo. The resulting oil was purified by flash chromatography eluting silica gel with hexane:EtOAc [4:1] to hexane:EtOAc [7:3] to give the title compound as a tan solid (730 mg, 80%); δ$_H$ (300 MHz, CDCl$_3$) 7.59 (1H, s, CH), 7.46 (1H, dd, Ar), 7.36 (1H, t, Ar), 7.02 (1H, dd, Ar).

Thieno[3,2-c]pyridin-7-ol

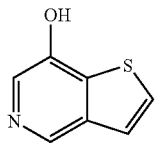

The title compound was prepared as described in Patent GB 2010249A.

Thieno[2,3-c]pyridin-4-ol

The title compound was prepared as described in Patent GB 2010249A.

4-Fluoro-2,3-dihydrobenz[b]thiophen-7-ol a) 5-(2-Fluoro-5-methoxybenzylidene)-2-thioxo-1,3-thiazolidin-4-one

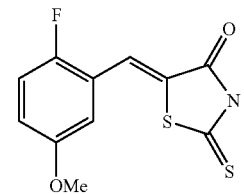

To a suspension of 2-fluoro-5-methoxybenzaldehyde (5.00 g, 32.46 mmol) and rhodanine (4.31 g, 32.46 mmol) in dry toluene (1000 mL) was added ammonium acetate (50 mg) and acetic acid (2 mL). The resulting suspension was allowed to stir at 120° C. for 12 h under Dean-Stark apparatus before being allowed to cool and filtered. Resultant solid was washed with hexane and allowed to dry in vacuo to give an orange crystalline solid (8.00 g, 91%); $\delta_H$ (300 MHz, CDCl$_3$) 7.50 (1H, s, CH=C); 7.31 (1H, t, Ar), 7.20-7.11 (1H, m Ar), 6.95-6.89 (1H, m, Ar), 3.80 (3H, s, OCH$_3$).

b) (2Z)-3-(2-Fluoro-5-methoxyphenyl)-2-mercapto-2-propenoic acid

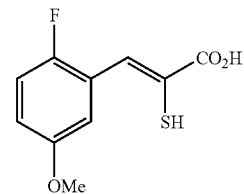

5-(2-Fluoro-5-methoxybenzylidene)-2-thioxo-1,3-thiazolidin-4-one (8.00 g, 9.7 mmol) was added in one portion to 25% w/v sodium hydroxide solution (40 mL). This was allowed stir at reflux for 1 h. After this time the reaction was allowed to cool to room temperature and poured onto water (50 mL). This was washed with dichloromethane (50 mL), and the aqueous layer acidified to pH 2 with aqueous hydrochloric acid (2 N, 50 mL) to give a white suspension. Product was extracted with ether (2×60 mL), dried (MgSO$_4$) and solvent removed in vacuo to give a white solid (6.71 g, 100%); $\delta_H$ (300 MHz, CD$_3$OD) 7.85 (1H, s, Ar), 7.46-7.35 (1H, m, Ar), 7.11 (1H, t, Ar), 7.01-6.75 (2H, m, CH=, and SH), 3.80 (3H, s, OCH$_3$).

c) 4-Fluoro-7-methoxy-1-benzothiophene-2-carboxylic acid

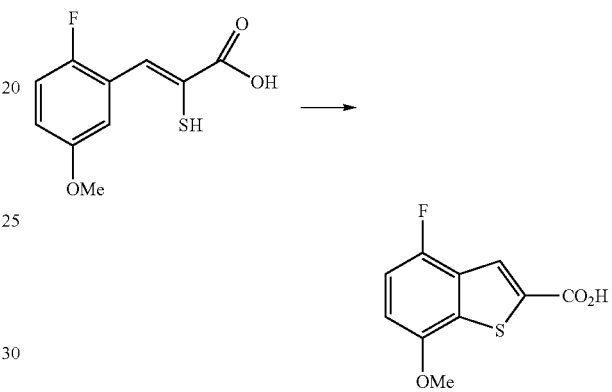

(2Z)-3-(2-Fluoro-5-methoxyphenyl)-2-mercapto-2-propenoic acid (1.00 g, 4.38 mmol) was added in one portion to a solution of iodine (1.66 g, 6.56 mmol) in dimethoxyethane (10 mL). This was heated in the microwave with 300 W at 160° C. for 10 mins. After this time the reaction was allowed to cool to room temperature and poured onto saturated sodium metabisulphite (200 mL) and ether (400 mL). Ether layer was separated and product extracted with aqueous sodium hydroxide (2 N, 2×100 mL). This was then acidified to pH 2 with aqueous hydrochloric acid (2 N, 250 mL), and product extracted with ether (2×150 mL). The combined organic extracts were dried (MgSO$_4$) and concentrated in vacuo to give a white solid (580 mg, 30%); $\delta_H$ (300 MHz, CD$_3$OD) 8.00 (1H, s, Ar), 7.30-7.19 (1H, m, Ar), 7.10-7.00 (1H, m, Ar), 3.95.(3H, s, OCH$_3$).

d) 4-Fluoro-7-methoxy-1-benzothiophene

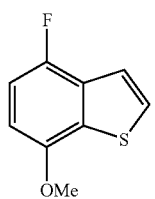

4-Fluoro-7-methoxy-1-benzothiophene-2-carboxylic acid (2.00 g, 8.84 mmol) was added in one portion to DBU (8 mL) and dimethyl acetamide (10 mL). This was heated in the microwave with 300 W at 200° C. for 1 h. The reaction mixture was allowed to cool and poured onto water (100 mL). Product was extracted with hexane (2×100 mL), washed with aqueous hydrochloric acid (2 N, 50 mL), aqueous sodium hydroxide (2 N, 50 mL), and the combined organic extracts were dried (MgSO$_4$) and concentrated in vacuo. The residue was purified by flash chromatography eluting silica gel with hexane:ethyl acetate [96:4] to give an oil (1.12 g, 70%): δ$_H$ (300 MHz, CDCl$_3$) 7.4 (2H, s, Ar), 6.9 (1H, t, Ar), 6.60 (1H, dd, Ar), 3.91 (3H, s, OCH$_3$).

e) 4-Fluoro-7-methoxy-2,3-dihydrobenzo[b]thiophene

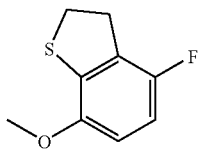

To a solution of 4-fluoro-7-methoxy-1-benzothiophene (1.55 g, 8.5 mmol, 1 eq) in trifluoroacetic acid (40 ml) was added triethylsilane (3.40 ml, 21.25 mmol, 2.5 eq). The mixture was heated to 60° C. for 48 hours, then cooled to room temperature and the solvent removed in vacuo. The crude product was purified by flash chromatography with a gradient of 40-60% chloroform in heptane to give 1.24 g, 80% recovered starting material and 199 mg, 13% yield of the title compound as a colourless oil: δ$_H$ (300 MHz, CDCl$_3$) 3.78-6.58 (2H, m, ArH), 3.82 (3H, s, CH$_3$) and 3.44-3.30 (4H, m, SCH$_2$CH$_2$).

f) 4-Fluoro-2,3-dihydrobenzo[b]thiophen-7-ol

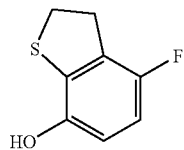

A BBr$_3$ demethylation of 4-fluoro-7-methoxy-2,3-dihydrobenzo[b]thiophene similar to that described for 4-hydroxy benzothiazole affords the title compound as a brown solid 251 mg: δ$_H$ (300 MHz, CDCl$_3$) 6.57-6.48 (2H, m, ArH), 4.67 (1H, br. s, OH) and 3.43-3.23 (4H, m, SCH$_2$CH$_2$).

4-[(3R)-3-Chloro-1-phenyl-propoxy]-isoquinoline

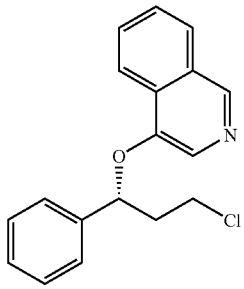

Add 4,4-(dimethyl-1,1-dioxido-1,2,5-thiadiazolidin-2-yl)-triphenyl phosphonium (547 mg, 1.4 mmol, 1.2 equiv. Prepared as described in *J. Org. Chem.* 1994, 59, 2289.) to a stirred solution of (S)-(−)-3-chloro-1-phenyl-1-propanol (306 mg, 1.17 mmol, 1 equiv.) and isoquinolin-4-ol (206 mg, 1.42 mmol, 1.2 equiv. prepared as described in *Tetrahedron*, 1963, 19, 827-832) in dry toluene (11 mL) and stir at room temperature for 18 hr. Add ethyl acetate, water, and brine, separate the layers, and extract the aqueous layer with ethyl acetate (3 times). Wash the combined organic extracts with brine (2 times), dry over anhydrous magnesium sulfate, filter, and concentrate under reduced pressure. Purification by medium pressure liquid chromatography eluting with 0-50% ethyl acetate in hexanes affords the title compound as a pale yellow oil (163 mg, 47%): δ$_H$ (CDCl$_3$, 400 MHz): 2.32-2.42 (m, 1H), 2.66-2.71 (m, 1H), 3.64-3.72 (m, 1H), 3.82-3.91 (m, 1H), 5.67 (dd, 1H, J=9, 5 Hz), 7.25-7.37 (m, 3H), 7.40-7.46 (m, 2H), 7.62 (ddd, 1H, J=7, 7, 2 Hz), 7.73 (ddd, 1H, J=7, 7, 1 Hz), 7.91 (d, 1H, J=8 Hz), 7.93 (s, 1H), 8.33 (dd, 1H, J=8, 1 Hz), 8.83 (s, 1H).

Similarly prepared were

6-[(3R)-3-Chloro-1-phenyl-propoxy]-isoquinoline

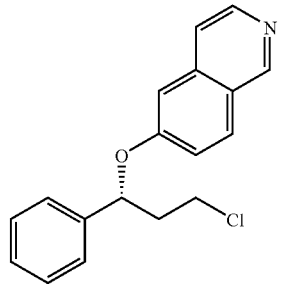

as a pale yellow oil: δ$_H$ (CDCl$_3$, 400 MHz): 2.25-2.35 (m, 1H), 2.50-2.60 (m, 1H), 3.60-3.69 (m, 1H), 3.80-3.90 (m, 1H), 5.58 (dd, 1H, J=9, 5 Hz), 6.96 (d, 1H, J=2 Hz), 7.23-7.47 (m, 7H), 7.84 (d, 1H, J=10 Hz), 8.36 (br s, 1H), 9.01 (br s, 1H).

5-[(3R)-3-Chloro-1-phenyl-propoxy]-[1,7]naphthyridine

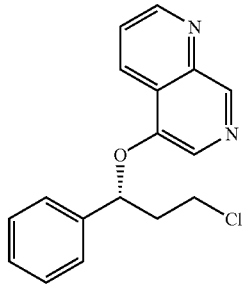

using [1,7]naphthyridin-5-ol (prepared as described in *Liebigs Annalen Der Chemie*, 1979, 443-445) affords the title compound as a gummy yellow oil (349 mg, 74%): δ$_H$(CDCl$_3$, 400 MHz): 2.32-2.43 (m, 1H), 2.60-2.71 (m, 1H), 3.60-3.67 (m, 1H), 3.78-3.87 (m, 1H), 5.67 (dd, 1H, J=8, 5 Hz), 7.25-7.45 (m, 5H), 7.63 (dd, 1H, J=9, 5 Hz), 8.02 (br s, 1H), 8.65 (dd, 1H, J=9, 1 Hz), 9.02 (dd, 1H, J=5, 1 Hz), 9.09 (br s, 1H).

5-[(3R)-3-Chloro-1-phenyl-propoxy]-isoquinoline

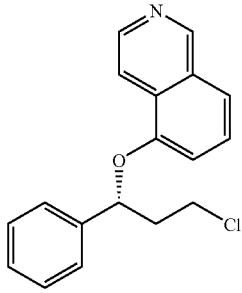

using 5-hydroxy isoquinoline (commercially available from the Aldrich Chemical Company) affords the title compound as a yellow oil (550 mg, 74%): $\delta_H$ (CDCl$_3$, 400 MHz): 2.31-2.42 (m, 1H), 2.60-2.70 (m, 1H), 3.64-3.72 (m, 1H), 3.82-3.91 (m, 1H), 5.63 (dd, 1H, J=8, 5 Hz), 6.89 (d, 1H, J=8 Hz), 7.26-7.44 (m, 6H), 7.51 (d, 1H, J=8 Hz), 8.18 (d, 1H, J=6 Hz), 8.57 (d, 1H, J=6 Hz), 9.21 (br d, 1H).

5-[(3R)-3-Chloro-1-phenyl-propoxy]-quinoline

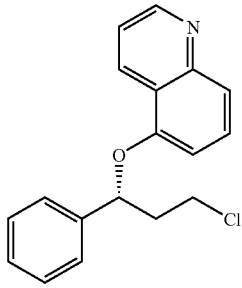

using 5-quinolinol (commercially available from the Aldrich Chemical Company) affords the title compound as a colorless foam (93 mg, 40%): $\delta_H$ (CDCl$_3$, 400 MHz): 2.24-2.34 (m, 1H), 2.52-2.62 (m, 1H), 3.55-3.63 (m, 1H), 3.74-3.82 (m, 1H), 5.54 (dd, 1H, J=8,4 Hz), 6.65 (d, 1H, J=8 Hz), 7.18-7.40 (m, 7H), 7.56 (d, 1H, J=8 Hz), 8.63 (ddd, 1H, J=8, 1, 1 Hz), 8.84 (dd, 1H, J=5, 2 Hz).

(1R)-4-Fluoro-7-(3-iodo-1-phenyl-propoxy)-2,3-dihydrobenzo[b]thiophene

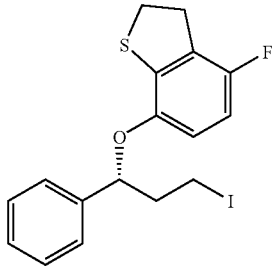

using (S)-1-iodo-3-phenyl-3-propanol with 4-fluoro-2,3-dihydrobenzo[b]thiophen-7-ol, to give 243 mg of the title compound as a colourless solid: $\delta_H$ (300 MHz, CDCl$_3$) 7.32-7.12 (5H, m, 3-ArH), 6.46-6.27 (3H, m, ArH), 5.15-5.06 (1H, m, CHO), 3.43-3.11 (6H, m CH$_2$CH$_2$HI and SCH$_2$CH$_2$), 2.50-2.31 (1H, m, CHHCH$_2$I) and 2.27-2.09 (1H, m, CHHCH$_2$I).

4-[(1R)-3-chloro-1-phenylpropyl]oxy-1-benzothiazole

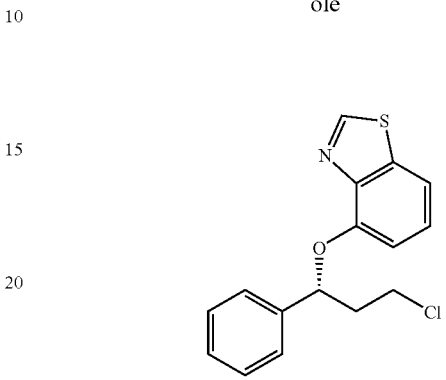

as a colourless oil (200 mg, 100%); R$_f$=0.40 in hexane:ether [1:1]: $\delta_H$ (300 MHz, CDCl$_3$) 8.95 (1H, s, Ar), 7.49-6.81 (8H, m, Ar), 5.73-5.68 (1H, m, CHO), 3.94-3.91 (1H, m, CH), 3.72-3.67 (1H, m, CH), 2.73-2.71 (1H, m, CHH), 2.40-2.30 (1H, m, CHH).

(3R)-3-(1,3-Benzothiazol-4-yloxy)-N-methyl-3-phenyl-N-(phenylmethyl)-propan-1-amine

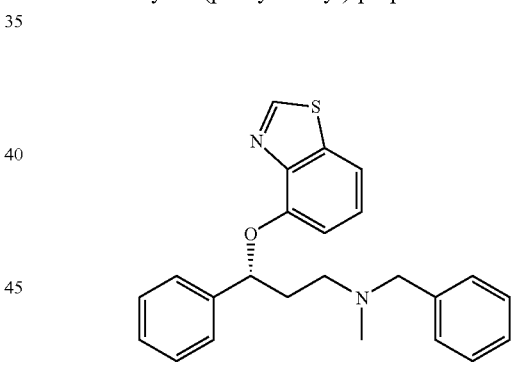

N-Methyl benzylamine (100 μl, 0.79 mmol) was added to a stirred suspension of 4-[(1R)-3-chloro-1-phenylpropyl]oxy-1-benzothiazole (200 mg, 0.658 mmol) and K$_2$CO$_3$ (450 mg, 3.29 mmol) and potassium iodide (110 mg, 0.658 mmol) in MeCN (20 ml). The resulting suspension was stirred at 60° C. for 48 hrs. After this time the reaction was allowed to cool to room temperature and diluted with water (ca. 50 ml) and extracted with EtOAc (3×50 ml). The combined organic extracts were dried (MgSO$_4$) and the solvent removed in vacuo. The resulting oil was purified by flash chromatography eluting silica gel with DCM:MeOH [97.5:2.5] to DCM:MeOH [9:1] to give the title compound as a tan oil (180 mg, 70%); R$_f$=0.40 in DCM:MeOH [9:1]: $\delta_H$ (300 MHz, CDCl$_3$) 8.90 (1H, s, Ar), 7.45-6.77 (13H, m, Ar), 5.64-5.59 (1H, m, CHO), 3.46 (2H, dd, CH$_2$), 2.78-2.68 (1H, m, CH), 2.53-2.44 (2H, m, CH$_2$), 2.21 (3H, s, CH$_3$), 2.14-2.11 (1H, m, CH).

7-[(1R)-(3-Chloro-1-phenyl-propoxy)]-thien[3,2-b]pyridine

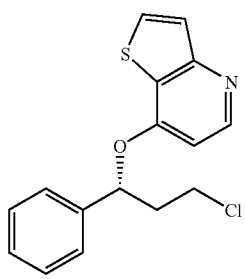

(S)-(−)-3-chloro-1-phenyl-1-propanol (1 g, 5.8 mmol) and thieno[3,2-b]pyridin-7-ol (1.15 g, 7.6 mmol, commercially available from the Aldrich Chemical Company) in dry TBF (6 ml) were stirred under an inert atmosphere of nitrogen. $PPh_3$ (1.99 g, 7.6 mmol) followed by DEAD (1 mL, 7.6 mmol) were added and the resulting solution was allowed to stir for a further 72 h while heating at 40° C. before the solvent was removed in vacuo. The residue was purified by flash chromatography, eluting silica gel with hexane:ethyl acetate [100:0 to 1:3] to yield the title compound (1.38 g, 78%); mass spectrum (ion spray): m/z=304.05 (m+1).

Prepared similarly was

7-[(1S)-(3-Chloro-1-phenyl-propoxy)]-thieno[3,2-b]pyridine

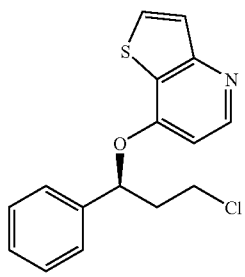

using (R)-(+)-3-chloro-1-phenyl-1-propanol, thieno[3,2-b]pyridin-7-ol (commercially available from the Aldrich Chemical Company), $PBu_3$, and ADPP gave the title compound (0.71 g, 54%); Mass spectrum (ion spray): m/z=304.06 (m+1).

7-[(1R)-(3-Iodo-1-phenyl-propoxy)]-thieno[3,2-b]pyridine

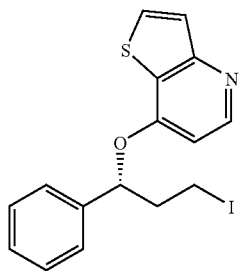

To a solution of 7-[(1R)-(3-Chloro-1-phenyl-propoxy)]-thieno[3,2-b]pyridine (703 mg, 2.3 mmol) in 15 mL of acetone was added NaI (3.5 g, 23 mmol). The resulting solution was allowed to stir at 55° C. for 18 h before removing the acetone in vacuo. The residue was taken up in $CH_2Cl_2$ and water. The layers were separated and the aqueous phase was further extracted 2 times with $CH_2Cl_2$. The combined organic phase was dried ($MgSO_4$) and concentrated in vacuo. The residue was purified by flash chromatography eluting silica gel with hexane:ethyl acetate [100:0 to 1:1] to yield the title compound (0.79 g, 87%); mass spectrum (ion spray): m/z=395.98 (m+1).

Prepared similarly was

7-[(1S)-(3-Iodo-1-phenyl-propoxy)]-thieno[3,2-b]pyridine

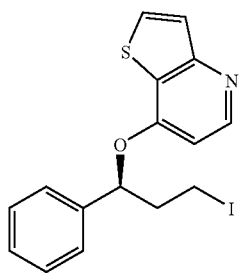

using 7-[(1S)-(3-chloro-1-phenyl-propoxy)]-thieno[3,2-b]pyridine gave the title compound (0.22 g, 71%); Mass spectrum (ion spray): m/z=395.99 (m+1).

4-[(3S)-3-Chloro-1-phenyl-propoxy]-isoquinoline

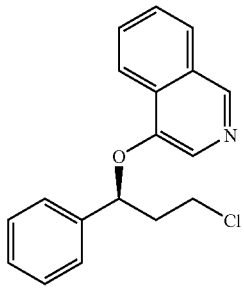

Add 4,4-(dimethyl-1,1-dioxido-1,2,5-thiadiazolidin-2-yl)-triphenyl phosphonium (790 mg, 2.0 mmol, 1.3 equiv.) to a stirred solution of (R)-(+)-3-chloro-1-phenyl-1-propanol (404 mg, 1.54 mmol, 1 equiv.) and isoquinolinfol (293 mg, 2.0 mmol, 1.3 equiv., prepared as described in *Tetrahedron*, 1963, 19, 827-832) in dry toluene (15 mL) and stir at room temperature for 18 hr. Add ethyl acetate, water, and brine, separate the layers, and extract the aqueous layer with ethyl acetate (3 times). Wash the combined organic extracts with brine (2 times), dry over anhydrous magnesium sulfate, filter, and concentrate under reduced pressure. Purification by medium pressure liquid chromatography eluting with 0-20% ethyl acetate in hexanes affords the title compound as a pale yellow oil (229 mg, 50%): $\delta_H$ (CDCl$_3$, 400 MHz): 2.32-2.42 (m, 1H), 2.66-2.71 (m, 1H), 3.64-3.72 (m, 1H), 3.82-3.91 (m, 1H), 5.67 (dd, 1H, J=9, 5 Hz), 7.25-7.37 (m, 3H), 7.40-7.46 (m, 2H), 7.62 (ddd, 1H, J=7, 7, 2 Hz), 7.73 (ddd, 1H, J=7, 7, 1 Hz), 7.91 (d, 1H, J=8 Hz), 7.93 (s, 1H), 8.33 (dd, 1H, J=8, 1 Hz), 8.83 (s, 1H).

Similarly prepared were

6-[(3S)-3-Chloro-1-phenyl-propoxy]-isoquinoline

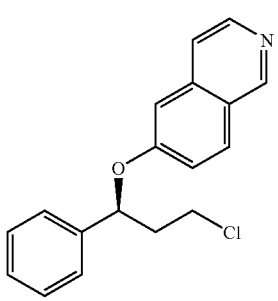

as a pale yellow oil: $\delta_H$ (CDCl$_3$, 400 MHz): 2.25-2.35 (m, 1H), 2.50-2.60 (m, 1H), 3.60-3.69 (m, 1H), 3.80-3.90 (m, 1H), 5.58 (dd, 1H, J=9, 5 Hz), 6.96 (d, 1H, J=2 Hz), 7.23-7.47 (m, 7H), 7.84 (d, 1H, J=10 Hz), 8.36 (br s, 1H), 9.01 (br s, 1H).

5-[(3S)-3-Chloro-1-phenyl-propoxy]-isoquinoline

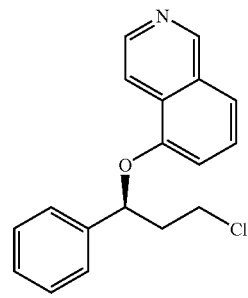

as a colorless oil (320 mg, 56%): $\delta_H$ (CDCl$_3$, 400 MHz): 2.31-2.42 (m, 1H), 2.60-2.70 (m, 1H), 3.64-3.72 (m, 1H), 3.82-3.91 (m, 1H), 5.63 (dd, 1H, J=8, 5 Hz), 6.89 (d, 1H, J=8 Hz), 7.26-7.44 (m, 6H), 7.51 (d, 1H, J=8 Hz), 8.18 (d, 1H, J=6 Hz), 8.57 (d, 1H, J=6 Hz), 9.21 (br d, 1H).

(1S)-4-Fluoro-7-(3-iodo-1-phenyl-propoxy)-2,3-dihydrobenzo[b]thiophene

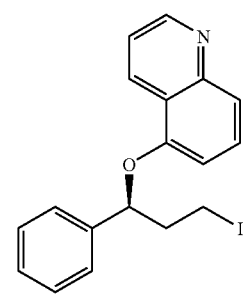

using (R)-1-iodo-3-phenyl-3-propanol with 4-fluoro-2,3-dihydrobenzo[b]thiophen-7-ol, to give 242 mg of the title compound as a colorless solid: $\delta_H$ (300 MHz, CDCl$_3$) 7.32-7.12 (5H, m, 3-ArH), 6.46-6.27 (3H, m, ArH), 5.15-5.06 (1H, m, CHO), 3.43-3.11 (6H, m, CH$_2$CH$_2$HI and SCH$_2$CH$_2$), 2.50-2.31 (1H, m, CHHCH$_2$I) and 2.27-2.09 (1H, m, CHHCH$_2$I).

5-[(3S)-3-Iodo-1-phenyl-propoxy]-quinoline

Add ADDP (434 mg, 1.72 mmol, 1.5 equiv.) to a stirred solution of of (R)-(+)-3-iodo-1-phenyl-1-propanol (404 mg, 1.54 mmol, 1 equiv.), tri-n-butyl phosphine (428 μl, 1.72 mmol, 1.5 equiv.), and 5-hydroxyisoquinoline (249 mg, 1.72 mmol, 1.5 equiv., commercially available from the Aldrich Chemical Company) in dry toluene (17 mL) and stir at room temperature overnight. The reaction mixture is concentrated under reduced pressure and the crude residue thus obtained is purified via medium pressure liquid chromatography eluting with 1:1 ethyl acetate:hexanes to afford the title compound as a yellow solid (298 mg, 67%): $\delta_H$ (CDCl$_3$, 400 MHz): 2.40-2.50 (m, 1H), 2.62-2.72 (m, 1H), 3.25-3.35 (m, 1H), 3.38-3.48 (m, 1H), 5.50 (dd, 1H, J=8,4 Hz), 6.73 (d, 1H, J=8 Hz), 7.23-7.49 (m, 7H), 7.66 (d, 1H, J=8 Hz), 8.73 (d, 1H, J=9 Hz), 8.92 (dd, 1H, J=4, 2 Hz).

In the following section, there is described the synthesis of compounds of the present invention.

EXAMPLE 1

[(3R)-3-(Isoquinolin-4-yloxy)-3-phenyl-propyl]-methyl-amine hydrochloride

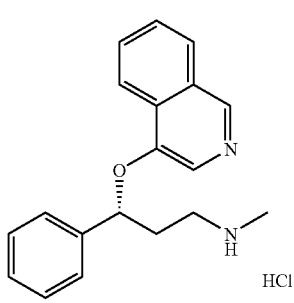

Add methyl amine (3 mL, 40% wt in water) to a solution of 4-[(3R)-chloro-1-phenyl-propoxy]-isoquinoline (163 mg, 0.546 mmol) in 1,4-dioxane (7 mL) in a heavy walled screw top sealed tube, seal the tube, and heat at 110° C. overnight. The mixture is cooled and concentrated under reduced pressure. Purification by medium pressure liquid chromatography eluting with 0-5% of 2N NH$_3$/MeOH in dichloromethane is followed by HCl salt formation by dissolving in methanol (5 mL), adding solid ammonium chloride (23.4 mg, 0.437 mmol,) and sonicating for 15-20 minutes. The mixture is concentrated under reduced pressure and the residue is dissolved in water, frozen at −78° C., and freeze dried to afford the title compound as a colorless solid (143 mg, 80%): $\delta_H$ (CDCl$_3$, 400 MHz): 2.50-2.62 (m, 1H), 2.67 (s, 3H), 2.70-2.81 (m, 1H), 3.17-3.27 (m, 2H), 5.75 (dd, 1H, J=8, 5 Hz), 7.19-7.30 (m, 3H), 7.41 (d, 2H, J=6 Hz), 7.59 (dd, 1H, J=7,7 Hz), 7.74 (dd, 1H, J=8, 8 Hz), 7.84 (d, 1H, J=8 Hz), 7.93 (s, 1H), 8.32 (d, 1H, J=8 Hz), 8.73 (s, 1H), 9.88 (br s, 2H).

Similarly prepared were

EXAMPLE 2

[(3R)-3-(Isoquinolin-6-yloxy)-3-phenyl-propyl]-methyl-amine hydrochloride

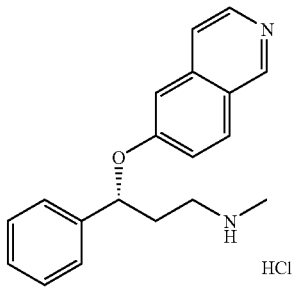

as an off-white solid (172 mg, 40%): $\delta_H$ (CDCl$_3$, 400 MHz): 2.43-2.63 (m, 2H), 2.66 (s, 3H), 3.10-3.25 (m, 2H), 5.62 (dd, 1H, J=8, 4 Hz), 6.91 (d, 1H, J=2 Hz), 7.20-7.43 (m, 7H), 7.78 (d, 1H, J=10 Hz), 8.32 (d, 1H, J=6 Hz), 9.01 (s, 1H).

EXAMPLE 3

Methyl-[(3R)-3-([1,7]naphthyridin-5-yloxy)-3-phenyl-propyl]-amine hydrochloride

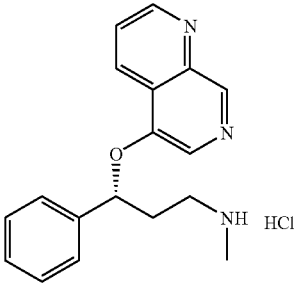

as a solid (175 mg, 32%): $\delta_H$ (CDCl$_3$, 400 MHz): 2.50-2.65 (m, 1H), 2.68-2.82 (m, 1H), 2.69 (s, 3H), 3.15-3.30 (m, 2H), 5.79 (dd, 1H, J=8, 5 Hz), 7.20-7.33 (m, 3H), 7.37-7.47 (m, 2H), 7.61 (dd, 1H, J=9, 4 Hz), 8.06 (br s, 1H), 8.66 (dd, 1H, J=9, 1 Hz), 8.98 (dd, 1H, J=4, 1 Hz), 9.00 (br s, 1H), 9.83 (br s 2H).

EXAMPLE 4

[(3R)-3-(Isoquinolin-5-yloxy)-3-phenyl-propyl]-methyl-amine hydrochloride

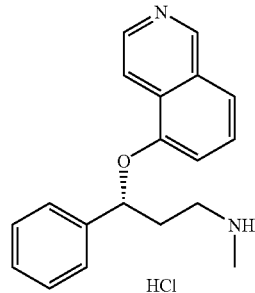

as a solid (211 mg, 50%): δ$_H$ (CDCl$_3$, 400 MHz): 2.50-2.63 (m, 1H), 2.64-2.80 (m, 1H), 2.67 (s, 3H), 3.15-3.30 (m, 2H), 5.69 (dd, 1H, J=8, 5 Hz), 6.86 (d, 1H, J=8 Hz), 7.20-7.33 (m, 4H), 7.38 (d, 2H, J=7 Hz), 7.45 (d, 1H, J=8 Hz), 8.16 (br s, 1H), 8.53 (br s, 1H), 9.20 (br s, 1H), 9.85 (br s, 2H).

EXAMPLE 5

Methyl-[(3R)-3-phenyl-3-(quinolin-5-yloxy)-propyl]-amine hydrochloride

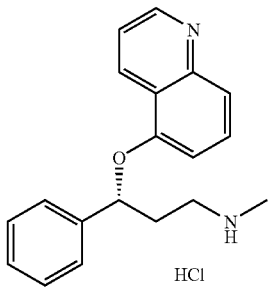

as a solid (149 mg, 71%): δ$_H$ (CDCl$_3$, 400 MHz): 2.51-2.78 (m, 2H), 2.64 (s, 3H), 3.15-3.27 (m, 2H), 5.63 (dd, 1H, J=8, 4 Hz), 6.70 (d, 1H, J=8 Hz), 7.20-7.50 (m, 7H), 7.63 (d, 1H, J=9 Hz), 8.74 (d, 1H, J=8 Hz), 8.84 (br d, 1H, J=3 Hz), 9.82 (br s, 2H).

EXAMPLE 6

(3R)-[3-(4-Fluoro-2,3-dihydrobenzo[b]thiopohen-7-yloxy)-3-phenylpropyl]-methyl-amine hydrochloride

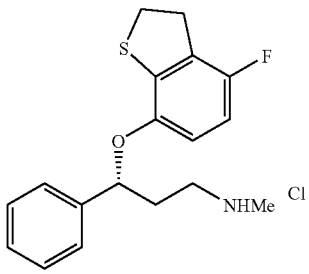

Prepared similarly except the aqueous methyl amine (40 wt %) was stirred at room temperature with (1R)-4-fluoro-7-(3-iodo-1-phenyl-propoxy)-2,3-dihydrobenzo[b]thiophene in THF. The hydrochloride salt was formed by addition of 1M hydrochloric acid in diethyl ether (1 eq) to a solution of the compound in diethyl ether. Filtration of the solid gave 111 mg of a white crystalline solid: δ$_H$ (300 MHz, CDCl$_3$) 9.61 (1H, br. s, NH), 7.41-7.20 (5H, m, ArH), 6.51-6.32 (2H, m, ArH), 5.40-5.32 (1H, m, CHO), 3.47-3.25 (4H, m, SCH$_2$CH$_2$), 3.25-3.15 (2H, m, 1-CH$_2$), 2.70 (3H, s, NHCH$_3$) and 2.58-2.31 (2H, m, 2-CH$_2$).

Prepared similarly was

EXAMPLE 7

(3S)-[3-(4-Fluoro-2,3-dihydrobenzo[b]thiophen-7-yloxy-3-phenylpropyl]-methyl-amine hydrochloride

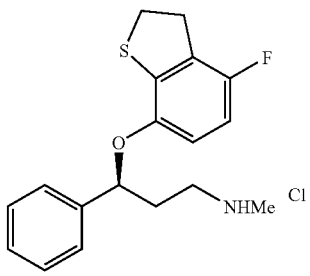

to give 101 mg of a white crystalline solid; δ$_H$ (300 MHz, CDCl$_3$) 9.61 (1H, br. s, NH), 7.41-7.20 (5H, m, ArH), 6.51-6.32 (2H, m, ArH), 5.40-5.32 (1H, m, CHO), 3.47-3.25 (4H, m, SCH$_2$CH$_2$), 3.25-3.15 (2H, m, 1-CH$_2$), 2.70 (3H, s, NHCH$_3$) and 2.58-2.31 (2H, m, 2-CH$_2$).

EXAMPLE 8

(3R)-3-(1,3-Benzothiazol-4-yloxy)-N-methyl-3-phenyl-propan-1-amine

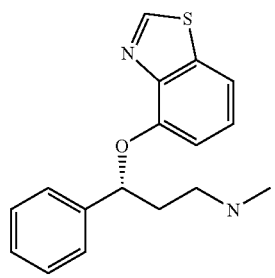

To a stirred suspension of (3R)-3-(1,3-benzothiazol-4-yloxy)-N-methyl-3-phenyl-N-(phenylmethyl)-propan-1-amine (0.18 g, 0.463 mmol) in dry DCM (10 ml) and Polymer supported diethylamine [PS-DIEA] (0.39 g, 3.56 mmol/g, 1.38 mmol) was added 1-chloroethyl chloroformate (0.25 ml, 2.3 mmol), the resulting suspension was heated to reflux for 2 hours. The reaction mixture was allowed to cool to room temperature and the PS-DIEA was removed by filtration. The reaction mixture was concentrated in vacuo, with the residue being re-dissolved in MeOH (10 ml) and heated to reflux for a further 4 hours. After this time the reaction was concentrated in vacuo and purified by flash chromatography eluting silica gel with DCM:MeOH [9:1] to give the free base (136 mg, 98%). R$_f$=0.36 [9:1] DCM:MeOH: δ$_H$ (300 MHz, CDCl$_3$) 9.07 (1H, s, Ar), 7.60-6.66 (8H, m, Ar), 5.39 (1H, dd, CHO), 3.49-3.45 (1H, m, CHH), 3.31-3.20 (1H, m, CHH), 2.88 (3H, s, CH$_3$), 2.68-2.62 (1H, m, CHH), 2.51-2.47 (1H, m, CHH).

EXAMPLE 9

Methyl-[(3R)-3-phenyl-3-(thieno[3,2-b]pyridin-7-yloxy)-propyl]-amine hydrochloride

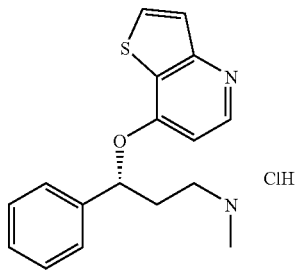

Methylamine (40% in water, 7 ml) was added to a solution of 7-[(1R)-(3-Iodo-1-phenyl-propoxy)]-thieno[3,2-b]pyridine (110 mg, 0.28 mmol) in EtOH (5 ml), the resulting solution was stirred at rt for 4 h. The solvent was removed in vacuo and the residue was purified by flash chromatography eluting silica gel with $CH_2Cl_2$:MeOH (2M $NH_3$) [100:0 to 10:1] to yield the free-base of the title compound (153 mg, 77%). The resulting residue was dissolved in MeOH (5 mL) and $NH_4Cl$ was added. The mixture was sonicated at room temperature for 10 min and then the solvent removed in vacuo. The residue was dissolved in MeCN (0.5 mL) and water (1 mL), this solution was then frozen by immersion in a dry ice:acetone bath, the resulting frozen material was freeze dried overnight to yield the target compound as a fluffy white solid: Melting point of title compound: 120.4° C.

Prepared similarly were

EXAMPLE 10

Methyl-[(3S)-3-phenyl-3-(thieno[3,2-b]pyridin-7-yloxy)-propyl]-amine hydrochloride

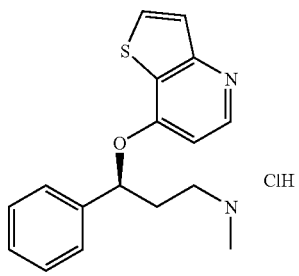

to afford the title compound (120 mg, 80%); Melting point: 118.2° C.

EXAMPLE 11

Methyl-[(3S)-3-phenyl-3-(thieno[3,2-c]pyridin-7-yloxy)-propyl]-amine hydrochloride

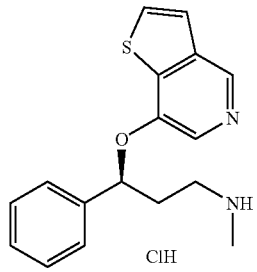

(R)-(+)-3-iodo-1-phenyl-1-propanol (0.68 g, 2.6 mmol) and thieno[3,2-c]pyridin-7-ol (0.30 g, 1.98 mmol) in dry THF (8 ml) were stirred under an inert atmosphere of nitrogen. Merck Reagent (4,4-(dimethyl-1,1-dioxido-1,2,5-thiadiazolidin-2-yl)-triphenyl phosphonium) (1.06 g, 2.6 mmol) was added and the resulting suspension was allowed to stir for a further 120 h at rt before the solvent was removed in vacuo. The residue was purified by flash chromatography, eluting silica gel with hexane: ethyl acetate [100:0 to 1:1] to yield the intermediate iodo compound (0.183 g, 23%). This residue was immediately taken up in 10 mL of 2M $NH_3$ in THF and stirred for 4 h. The solvent was removed in vacuo and the residue was purified by flash chromatography eluting silica gel with $CH_2Cl_2$:MeOH (2M $NH_3$) [100:0 to 3:1] to yield the free-base of the title compound (29.2 mg, 22%). The resulting residue was dissolved in MeOH (5 mL) and $NH_4Cl$ was added. The mixture was sonicated at room temperature for 10 min and then the solvent removed in vacuo. The residue was dissolved in MeCN (0.5 mL) and water (1 mL), this solution was then frozen by immersion in a dry ice:acetone bath, the resulting frozen material was freeze dried overnight to yield the target compound as a fluffy white solid: mass spectrum (ion spray): m/z=299.12 (m+1).

Prepared similarly were

EXAMPLE 12

Methyl-[(3R)-3-phenyl-3-(thieno[3,2-c]pyridin-7-yloxy)-propyl]-amine hydrochloride

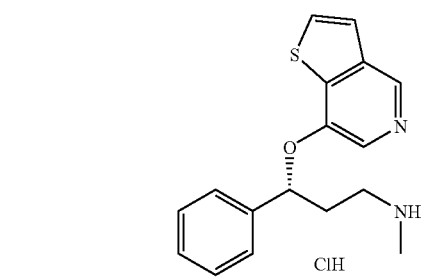

gave the title compound (49.5 mg, 41%); mass spectrum (ion spray): m/z=299.12 (m+1).

EXAMPLE 13

Methyl-[(3R)-3-phenyl-3-(thieno[2,3-c]pyridin-4-yloxy)-propyl]-amine hydrochloride

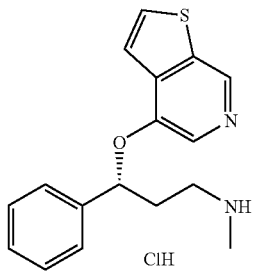

gave the title compound as a solid (38 mg, 29%): Melting point: 68.1° C.

EXAMPLE 14

(S)-[3-(Benzo[d]isothiazol-4-yloxy)-3-phenyl-propyl]-methyl-amine hydrochloride

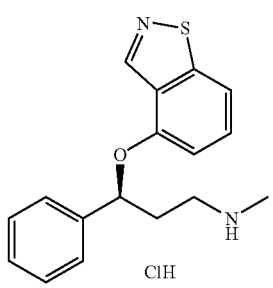

gave the title compound (206 mg, 62%): Mass spectrum (ion-spray): m/z=299.1 (m+1).

EXAMPLE 15

(R)-[3-(Benzo[d]isothiazol-7-yloxy)-3-phenyl-propyl]-methyl-amine hydrochloride

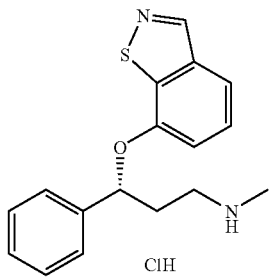

gave the title compound (17 mg, 22%); Mass spectrum (ion-spray): m/z=299.1 (m+1).

EXAMPLE 16

(S)-[3-(Benzo[d]isothiazole-7-yloxy)-3-phenyl-propyl]-methyl-amine hydrochloride

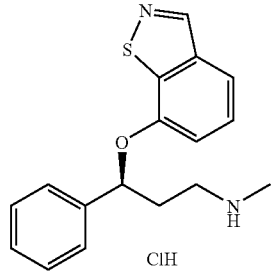

gave the title compound (85 mg, 50%); Mass spectrum (ion-spray): m/z=299.1 (m+1).

EXAMPLE 17

(R)-Methyl-[3-(7-methyl-benzo[d]isothiazol-4-yloxy)-3-phenyl-propyl]-amine hydrochloride

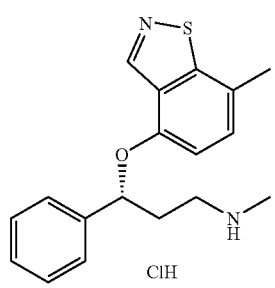

gave the title compound (77 mg, 32%); Mass spectrum (ion-spray): m/z=313.1 (M+1).

EXAMPLE 18

(S)-Methyl-[3-(7-methyl-benzo[d]isothiazol-4-yloxy)-3-phenyl-propyl]-amine hydrochloride

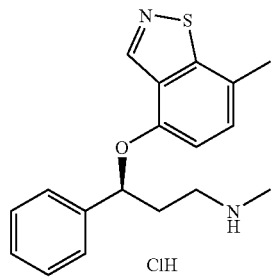

gave the title compound (71 mg, 34%); Mass spectrum (ion-spray): m/z=313.1 (m+1).

EXAMPLE 19

[(3S)-3-(Isoquiolin-4-yloxy)-3-phenyl-propyl]-methyl-amine hydrochloride

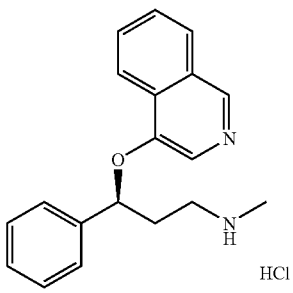

Add methyl amine (3 mL, 40% wt in water) to a solution of 4-[(3S)-chloro-1-phenyl-propoxy]-isoquinoline (229 mg, 0.769 mmol) in 1,4-dioxane (10 mL) in a heavy walled screw top sealed tube, seal the tube, and heat at 110° C. overnight. The mixture is cooled and concentrated under reduced pressure. Purification by medium pressure liquid chromatography eluting with 0-4% of 2N NH$_3$/MeOH in dichloromethane is followed by HCl salt formation by dissolving in methanol (3 mL), adding solid ammonium chloride (30.8 mg, 0.576 mmol,) and sonicating for 15-20 minutes. The mixture is concentrated under reduced pressure and the residue is dissolved in water, frozen at −78° C., and freeze dried to afford the title compound as a colorless solid (185 mg, 73%): δ$_H$ (CDCl$_3$, 400 MHz): 2.50-2.62 (m, 1H), 2.67 (s, 3H), 2.70-2.81 (m, 1H), 3.17-3.27 (m, 2H), 5.75 (dd, 1H, J=8, 5 Hz), 7.19-7.30 (m, 3H), 7.41 (d, 2H, J=6 Hz), 7.59 (dd, 1H, J=7, 7 Hz), 7.74 (dd, 1H, J=8, 8 Hz), 7.84 (d, 1H, J=8 Hz), 7.93 (s, 1H), 8.32 (d, 1H, J=8 Hz), 8.73 (s, 1H), 9.88 (br s, 2H).

Similarly prepared were

EXAMPLE 20

[(3S)-3-(Isoquinolin-6-yloxy)-3-phenyl-propyl]-methyl-amine hydrochloride

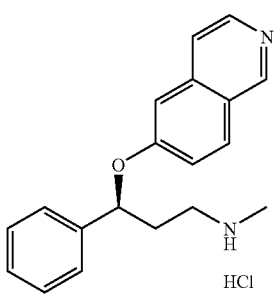

as an off-white solid (270 mg, 37%): δ$_H$ (CDCl$_3$, 400 MHz): 2.43-2.63 (m, 2H), 2.66 (s, 3H), 3.10-3.25 (m, 2H), 5.62 (dd, 1H, J=8,4 Hz), 6.91 (d, 1H, J=2 Hz), 7.20-7.43 (m, 7H), 7.78 (d, 1H, J=10 Hz), 8.32 (d, 1H; J=6 Hz), 9.01 (s, 1).

EXAMPLE 21

[(3S)-3-(Isoquinolin-5-yloxy)-3-phenyl-propyl]-methyl-amine hydrochloride

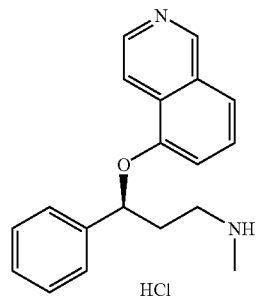

as a solid (358 mg, 98%): δ$_H$ (CDCl$_3$, 400 MHz): 2.50-2.63 (m, 1H), 2.64-2.80 (m, 1H), 2.67 (s, 3), 3.15-3.30 (m, 2H), 5.69 (dd, 1H, J=8, 5 Hz), 6.86 (d, 1H, J=8 Hz), 7.20-7.33 (m, 4H), 7.38 (d, 2H, J=7 Hz), 7.45 (d, 1H, J=8 Hz), 8.16 (br s, 1H), 8.53 (br s, 1H), 9.20 (br s, 1H), 9.85 (br s, 2H).

EXAMPLE 22

Methyl-[(3S)-3-phenyl-3-(quinolin-5-yloxy)-propyl]-amine hydrochloride

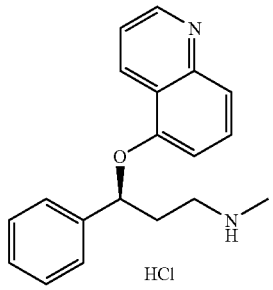

Add methyl amine (40% wt in water, 5 mL) to a solution of 5-[(3S)-iodo-1-phenyl-propoxy]-quinoline quinoline (200 mg, 0.51 mmol, 1 equiv.) in THF (1 mL) and stir at room temperature for 1 hr. The reaction mixture is concentrated under reduced pressure and purified by medium pressure liquid chromatography eluting with 0-8% of 2N NH$_3$/MeOH in dichloromethane which is followed by HCl salt formation by dissolving in methanol, adding solid ammonium chloride (9.5 mg, 0.18 mmol) and sonicating for 15-20 minutes. The mixture is concentrated under reduced pressure and the residue is dissolved in water, frozen at −78° C., and freeze dried to afford the title compound as a solid (65 mg, 35 %): δ$_H$ (CDCl$_3$, 400 MHz): 2.51-2.78 (m, 2H), 2.64 (s, 3H), 3.15-3.27 (m, 2H), 5.63 (dd, 1H, J=8, 4 Hz), 6.70 (d, 1H, J=8 Hz), 7.20-7.50 (m, 7H), 7.63 (d, 1H, J=9 Hz), 8.74 (d, 1H, J=8 Hz), 8.84 (br d, 1H, J=3 Hz), 9.82 (br s, 2H).

The compounds of the present invention may be used as medicaments in human or veterinary medicine. The compounds may be administered by various routes, for example, by oral or rectal routes, topically or parenterally, for example by injection, and are usually employed in the form of a pharmaceutical composition.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, solutions, syrups, aerosol (as a solid or in a liquid medium), ointments containing, for example, up to 10% by weight of the active compound, soft and hard gelatin capsules, suppositories, injection solutions and suspensions and sterile packaged powders.

Some examples of suitable carriers are lactose, dextrose, vegetable oils, benzyl alcohols, alkylene glycols, polyethylene glycols, glycerol triacetate, gelatin, carbohydrates such as starch and petroleum jelly, sucrose sorbitol, mannitol, starches, gum acacia, calcium phosphate, alginates, tragacanth, gelatin, syrup, methyl cellulose, methyl- and propylhydrobenzoate, talc, magnesium stearate and mineral oil. The compounds of formula (I) can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary doses for human subjects and other mammals, each unit containing a predetermined quantity of active material calculated to produce the desired therapeutic effect, in association with a suitable pharmaceutical carrier.

The pharmacological profile of the present compounds may be demonstrated as follows. Preferred compounds of the present invention exhibit a $K_i$ value less than 1 µM at the serotonin and norepinephrine transporters as determined using the scintillation proximity assays described below. More preferred compounds of the present invention exhibit a $K_i$ value less than 100 nM at the serotonin transporter and/or a $K_i$ value less than 100 nM at the norepinephrine transporter as determined using the scintillation proximity assays described below. Still more preferred compounds of the present invention are those which exhibit a $K_i$ value less than 100 nM (preferably less than 50 nM) at the serotonin transporter and a $K_i$ value less than 100 nM (preferably less than 50 nM) at the norepinephrine transporter as determined using the scintillation proximity assays described below. Furthermore, preferred compounds of the present invention selectively inhibit the serotonin and norepinephrine transporters relative to the dopamine transporter by a factor of at least five using the scintillation proximity assays as described below.

Generation of Stable Cell-lines Expressing the Human Dopamine, Norepinephrine and Serotonin Transporters Standard molecular cloning techniques were used to generate stable cell-lines expressing the human dopamine, norepinephrine and serotonin transporters. The polymerase chain reaction (PCR) was used in order to isolate and amplify each of the three full-length cDNAs from an appropriate cDNA library. Primers for PCR were designed using the following published sequence data:

Human dopamine transporter: GenBank M95167. Reference: Vandenbergh D J, Persico A M and Uhl G R. *A human dopanmine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Peng T, Chang A S, Ganapathy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products were cloned into a mammalian expression vector (eg pcDNA3.1 (Invitrogen)) using standard ligation techniques. The constructs were then used to stably transfect HEK293 cells using a commercially available lipofection reagent (Lipofectamine™—Invitrogen) following the manufacture's protocol.

Scintillation Proximity Assays for Determining the Affinity of Test Ligands at the Norepinephrine and Serotonin Transporters.

The compounds of the present invention are norepinephrine and serotonin reuptake inhibitors, and possess excellent activity in, for example, a scintillation proximity assay (e.g. J. Gobel, D. L. Saussy and A. Goetz, J. Pharmacol. Toxicolo. (1999), 42, 237-244). Thus $^3$H-nisoxetine binding to norepinephrine re-uptake sites in a cell line transfected with DNA encoding human norepinephrine transporter binding protein and similarly $^3$H-citalopram binding to serotonin re-uptake sites in a cell line transfected with DNA encoding human serotonin transporter binding protein have been used to determine the affinity of ligands at the norepinephrine and serotonin transporters respectively.

Norepinephrine Binding Assay

Membrane Preparation:

Cell pastes from large scale production of HEK-293 cells expressing cloned human norepinephrine transporters were homogenized in 4 volumes 50 mM Tris-HCl containing 300 mM NaCl and 5 mM KCl, pH 7.4. The homogenate was centrifuged twice (40,000 g, 10 min, 4° C.) with pellet re-suspension in 4 volumes of Tris-HCl buffer containing the above reagents after the first spin and 8 volumes after the second spin. The suspended homogenate was centrifuged (100 g, 10 min, 4° C.) and the supernatant kept and recentrifuged (40,000 g, 20 min, 4° C.). The pellet was resuspended in Tris-HCl buffer containing the above reagents along with 10% w/v sucrose and 0.1 mM phenylmethylsulfonyl fluoride (PMSF). The membrane preparation was stored in aliquots (1 ml) at −80° C. until required. The protein concentration of the membrane preparation was determined using a bicinchoninic acid (BCA) protein assay reagent kit (available from Pierce).

[³H]-Nisoxetine Binding Assay:

Each well of a 96 well microtitre plate was set up to contain the following:

50 μl 2 nM [N-methyl-³H]-Nisoxetine hydrochloride (70-87 Ci/mmol, from NEN Life Science Products)
75 μl Assay buffer (50 mM Tris-HCl pH 7.4 containing 300 mM NaCl and 5 mM KCl)
25 μl Test compound, assay buffer (total binding) or 10 μM Desipramine HCl (non-specific binding)
50 μl Wheatgerm agglutinin coated poly (vinyltoluene) (WGA PVT) SPA Beads (Amersham Biosciences RPNQ0001) (10 mg/ml)
50 μl Membrane (0.2 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki values for each of the test compounds.

Serotonin Binding Assay

The ability of a test compound to compete with [³H]-citalopram for its binding sites on cloned human serotonin transporter containing membranes has been used as a measure of test compound ability to block serotonin uptake via its specific transporter (Ramamoorthy, S., Giovanetti, E., Qian, Y., Blakely, R., (1998) J. Biol. Chem. 273, 2459).

Membrane Preparation:

Membrane preparation is essentially similar to that for the norepinephrine transporter containing membranes as described above. The membrane preparation was stored in aliquots (1 ml) at −70° C. until required. The protein concentration of the membrane preparation was determined using a BCA protein assay reagent kit.

[³H]-Citalopram Binding Assay:

Each well of a 96 well microtitre plate was set up to contain the following:

50 μl 2 nM [³H]-Citalopram (60-86 Ci/mmol, Amersham Biosciences)
75 μl Assay buffer (50 mM Tris-HCl pH 7.4 containing 150 mM NaCl and 5 mM KCl)
25 μl Diluted compound, assay buffer (total binding) or 100 μM Fluoxetine (non-specific binding)
50 μl WGA PVT SPA Beads (40 mg/ml)
50 μl Membrane preparation (0.4 mg protein per ml)

The microtitre plates were incubated at room temperature for 10 hours prior to reading in a Trilux scintillation counter. The results were analysed using an automatic spline fitting programme (Multicalc, Packard, Milton Keynes, UK) to provide Ki (nM) values for each of the test compounds.

Dopamine Binding Assay

The ability of a test compound to compete with [³H]-WIN35,428 for its binding sites on human cell membranes containing cloned human dopamine transporter has been used as a measure of the ability of such test compounds to block dopamine uptake via its specific transporter (Ramamoorthy et al 1998 supra).

Membrane Preparation:

Is essentially the same as for membranes containing cloned human serotonin transporter as described above.

[³H]-WIN35,428 Binding Assay:

Each well of a 96 well microtitre plate was set up to contain the following:

50 μl 4 nM [³H]-WIN35,428 (84-87 Ci/mmol, from NEN Life Science Products)
75 μl Assay buffer (50 nM Tris-HCl pH 7.4 containing 150 mM NaCl and 5 mM KCl)
25 μl Diluted compound, assay buffer (total binding) or 100 μM Nomifensine (non-specific binding)
50 μl WGA PVT SPA Beads (10 mg/ml)
50 μl Membrane preparation (0.2 mg protein per ml.)

The microtitre plates were incubated at room temperature for 120 minutes prior to reading in a Trilux scintillation counter. The results were analysed using an automatic spline fitting programme (Multicalc, Packard, Milton Keynes, UK) to provide Ki values for each of the test compounds.

Formalin Paw Assay

The analgesic effect of compounds of the invention for the treatment of persistent nociceptive pain was demonstrated using the well-known "formalin test." The formalin test is a model of persistent nociceptive activation induced by tissue injury which can lead to central sensitization. (Shibata, M., Ohkubo, T., Takahashi, H., and Inoki, R., "Modified formalin test: Characteristic biphasic pain response," *Pain* (1989) 38: 347-352; and Tjolsen, A., Berge, O. G., Hunskaar, S., Rosland, J. H., and Hole, K., "The formalin test: an evaluation of the method," *Pain* (1992) 51:5-17.) The effect of compounds of the invention on formalin-induced paw-licking behavior in the rat was investigated as an index of persistent nociceptive activation. In this test, the injection of formalin under the skin on the dorsal lateral surface of the hind paw of rats causes an immediate and intense increase in the spontaneous activity of C fiber afferents. This activation evokes a distinctly quantifiable behavior indicative of pain, such as licking of the injected paw. The behavioral response to formalin is biphasic, with an early phase that is short lived, followed by an extended tonic response or late phase of persistent nociceptive activation. Mechanisms causing the late phase response, such as central sensitization of pain transmitting neurons, are currently believed to contribute to various types of persistent pains.

Male Sprague-Dawley rats (200-250 g; Charles River, Portage, Md. were maintained at constant temperature and light (12 h light/12 h dark) for 4-7 days prior to the studies. Animals had free access to food and water at all times prior to the day of the experiment.

Scoring in the formalin test was performed according to Coderre et al., 1993b and Abbott et al., 1995. (Coderre T. J., Fundytus M. E., McKenna J. E., Dalal S. and Melzack R. "The formalin test: a validation of the weighted-scores method of the behavioral pain rating," *Pain*(1993b) 54: 43-50; and Abbott F. V., Franklin K. B. J. and Westbrook R. F. "The formalin test: scoring properties of the first and second phases of the pain response in rats," *Pain* (1995) 60: 91-102.) The sum of time spent licking in seconds from time 0 to 5 minutes was considered the early phase while the late phase was taken as the sum of seconds spent licking from 15 to 40 minutes.

Data are presented as means with standard errors of means (±SEM). Data were evaluated by one-way analysis of variance (ANOVA) and the appropriate contrasts analyzed by Tukey's test and Dunnett "t" test for two-sided comparisons.

The preferred compounds of the present invention show good stability to the action of the CYP 2D6 enzyme. This is advantageous because it is likely to lead to improved metabolic stability of the compounds.

Stability to the CYP 2D6 enzyme may be determined according to the assay described below:

In Vitro Determination of the Interaction of Compounds with CYP2D6 in Human Hepatic Microsomes Cytochrome P450 2D6 (CYP2D6) is a mammalian enzyme which is commonly associated with the metabolism of around 30% of pharmaceutical compounds. Moreover, this enzyme shows a genetic polymorphism with as a consequence a presence in the population of poor and normal metabolizers. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) were acquired from Human Biologics (Scottsdale, Ariz., USA). Quinidine and β-NADPH (β-Nicotinamide Adenine Dinucleotide Phosphate, reduced form, tetrasodium salt) were purchased from Sigma (St Louis, Mo., USA). All the other reagents and solvents were of analytical grade. A stock solution of the new chemical entity (NCE) was prepared in a mixture of Acetonitrile/Water to reach a final concentration of acetonitrile in the incubation below 0.5%.

The microsomal incubation mixture (total volume 0.1 mL) contained the NCE (4 µM), β-NADPH (1 mM), microsomal proteins (0.5 mg/mL), and Quinidine (0 or 2 µM) in 100 mM sodium phosphate buffer pH 7.4. The mixture was incubated for 30 minutes at 37° C. in a shaking waterbath. The reaction was terminated by the addition of acetonitrile (75 µL). The samples were vortexed and the denatured proteins were removed by centrifugation. The amount of NCE in the supernatant was analyzed by liquid chromatography/mass spectrometry (LC/MS) after addition of an internal standard. A sample was also taken at the start of the incubation (t=0), and analysed similarly.

Analysis of the NCE was performed by liquid chromatography/mass spectrometry. Ten µL of diluted samples (20 fold dilution in the mobile phase) were injected onto a Spherisorb CN Column, 5 µM and 2.1 mm×100 mm (Waters corp. Milford, Mass., USA). The mobile phase consisting of a mixture of Solvent A/Solvent B, 30/70 (v/v) was pumped (Alliance 2795, Waters corp. Milford, Mass., USA) through the column at a flow rate of 0.2 ml/minute. Solvent A and Solvent B were a mixture of ammonium formate $5.10^{-3}$ M pH 4.5/methanol in the proportions 95/5 (v/v) and 10/90 (v/v), for solvent A and solvent B, respectively. The NCE and the internal standard were quantified by monitoring their molecular ion using a mass spectrometer ZMD or ZQ (Waters-Micromass corp, Machester, UK) operated in a positive electrospray ionisation.

The extent of CYP2D6 involvement (% of CYP2D6 involvement) was calculated comparing the extent of metabolism in absence and in presence of quinidine in the incubation.

The extent of metabolism without inhibitor (%) was calculated as follows:

$$\frac{(NCE \text{ response in samples without inhibitor}) \text{time } 0 - (NCE \text{ response in samples without inhibitor}) \text{time } 30}{(NCE \text{ response in samples without inhibitor}) \text{time } 0} \times 100$$

The extent of metabolism with inhibitor (%) was calculated as follows:

$$\frac{(NCE \text{ response in samples without inhibitor}) \text{time } 0 - (NCE \text{ response in samples with inhibitor}) \text{time } 30}{(NCE \text{ response in samples without inhibitor}) \text{time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement was calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an IC$_{50}$ higher than 6 μM for CYP2D6 activity, the IC$_{50}$ being the concentration of the compound that gives 50% of inhibition of the CYP2D6 activity.

Material and Methods:

Human liver microsomes (mixture of 20 different donors, mixed gender) were acquired from Human Biologics (Scottsdale, Ariz.). β-NADPH was purchased from Sigma (St Louis, Mo.). Bufuralol was purchased from Ultrafine (Manchester, UK). All the other reagents and solvents were of analytical grade.

Microsomal incubation mixture (total volume 0.1 mL) contained bufuralol 10 μM, β-NADPH (2 mM), microsomal proteins (0.5 mg/mL), and the new chemical entity (NCE) (0, 5, and 25 μM) in 100 mM sodium phosphate buffer pH 7.4. The mixture was incubated in a shaking waterbath at 37° C. for 5 minutes. The reaction was terminated by the addition of methanol (75 μL). The samples were vortexed and the denaturated proteins were removed by centrifugation. The supernatant was analyzed by liquid chromatography connected to a fluorescence detector. The formation of the 1'-hydroxybufuralol was monitored in control samples (0 μM NCE) and in the samples incubated in presence of the NCE. The stock solution of NCE was prepared in a mixture of Acetonitrile/Water to reach a final concentration of acetonitrile in the incubation below 1.0%.

The determination of 1'hydroxybufuralol in the samples was performed by liquid chromatograhy with fluorimetric detection as described below. Twenty five μL samples were injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, was pumped through the column at a flow rate of 1 ml/min:

| Time (minutes) | Solvent A (%) | Solvent B (%) |
| --- | --- | --- |
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consisted of a mixture of 0.02 M potassium dihydrogenophosphate buffer pH3/methanol in the proportion 90/10 (v/v) for solvent A and 10/90 (v/v) for solvent B. The run time was 7.5 minutes. Formation of 1'-hydroxybufuralol was monitored by fluorimetric detection with extinction at λ 252 nm and emission at λ 302 nm.

The IC$_{50}$ of the NCE for CYP2D6 was calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1'\text{-hydroxybufuralol formed without inhibitor}) - (1'\text{-hydroxybufuralol formed with inhibitor})}{(1'\text{-hydroxybufuralol area formed without inhibitor})} \times 100$$

The IC$_{50}$ is calculated from the percent inhibition of the formation of the 1'-hydroxyfururalol as follows (assuming competitive inhibition):

$$\frac{NCE \text{ Concentration} \times (100 - \text{Percent of inhibition})}{\text{Percent of inhibition}}$$

The IC$_{50}$ estimation is assumed valid if inhibition is between 20% and 80% (Moody G C, Griffin S J, Mather A N, McGinnity D P, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula I:

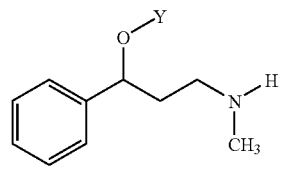

where Y is thienopyridinyl; or a pharmaceutically acceptable salt thereof.

2. A compound of claim 1, wherein the compound possesses the stereochemistry defined in formula II

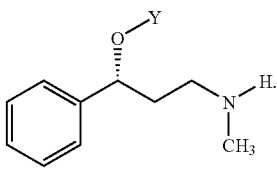

3. A compound claim 1, wherein the compound possesses the stereochemistry defined in formula III

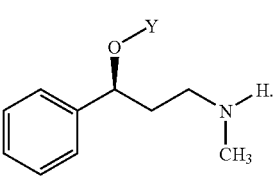

4. A pharmaceutical composition comprising a compound of formula I or a pharmaceutically acceptable salt thereof, as defined in claim 1, together with a pharmaceutically acceptable diluent or carrier.

* * * * *